United States Patent
Weihofen et al.

(10) Patent No.: US 10,301,381 B2
(45) Date of Patent: May 28, 2019

(54) ANTI-ALPHA SYNUCLEIN BINDING MOLECULES

(71) Applicants: Biogen International Neuroscience GmbH, Zug (CH); University of Zürich, Zürich (CH)

(72) Inventors: Andreas Weihofen, Belmont, MA (US); Jan Grimm, Dubendorf (CH); Christoph Hock, Erlenbach (CH); Roger Nitsch, Zumikon (CH); Lihe Su, Reading, MA (US); Paul Weinreb, Andover, MA (US)

(73) Assignees: Biogen International Neuroscience GmbH, Baar (CH); University of Zürich, Zürich (CH)

( * ) Notice: Subject to any disclaimer, the term of this patent is extended or adjusted under 35 U.S.C. 154(b) by 0 days.

(21) Appl. No.: 15/914,110

(22) Filed: Mar. 7, 2018

(65) Prior Publication Data
US 2018/0355027 A1   Dec. 13, 2018

Related U.S. Application Data

(62) Division of application No. 15/410,128, filed on Jan. 19, 2017, now Pat. No. 9,975,947, which is a division
(Continued)

(51) Int. Cl.
C07K 14/47 (2006.01)
A61P 25/16 (2006.01)
(Continued)

(52) U.S. Cl.
CPC .......... *C07K 16/18* (2013.01); *A61K 47/6849* (2017.08); *G01N 33/6896* (2013.01);
(Continued)

(58) Field of Classification Search
None
See application file for complete search history.

(56) References Cited

U.S. PATENT DOCUMENTS

| 5,676,950 A | 10/1997 | Small, Jr. et al. |
| 6,187,309 B1 | 2/2001 | McMichael et al. |
(Continued)

FOREIGN PATENT DOCUMENTS

| CA | 2746778 | 6/2010 |
| EP | 1185289 | 12/2000 |
(Continued)

OTHER PUBLICATIONS

"Aducanumab" [online]. Alzforum, by biomedical Research Forum, LLC, http://www.alzforum.org/therapeutics/aducanumab. Retrieved on Aug. 25, 2015, 5 pages.
(Continued)

*Primary Examiner* — Aurora M Fontainhas
(74) *Attorney, Agent, or Firm* — Fish & Richardson P.C.

(57) ABSTRACT

Provided are anti-human α-synuclein-specific binding molecules, e.g., antibodies or antiben-binding fragments, variants or derivatives thereof, as methods related thereto. Further provided are anti-human α-synuclein binding molecules which bind to specific N-terminal and C-terminal epitopes on human α-synuclein. The binding molecules described herein can be used in pharmaceutical and diagnostic compositions for α-synuclein targeted immunotherapy and diagnosis, respectively.

16 Claims, 6 Drawing Sheets

Specification includes a Sequence Listing.

```
NI-202.21D11-VH (variable heavy chain sequence VH; SEQ ID NO:15)
FR1-------------------------CDR1-FR2----------CDR2-------------
EVQLVESGAEVKKPGASVKVSCKASGYTFTNYAMHWVRQAPGQRLEWMGWINAGNGKRKYSQKFQD
FR3-------------------------CDR3----------JH--------
RVTINRDTSASTIYMELSSLGSEDTAVYYCAREEDHAGSGSYLSMDVWGQGTLVTVSS NI-202.21D11-VH-GL (GL (variable heavy chain sequence VH, corrected
according to the Germ Line Sequence; SEQ ID NO:20)
FR1-------------------------CDR1-FR2----------CDR2-------------
QVQLVQSGAEVKKPGASVKVSCKASGYTFTNYAMHWVRQAPGQRLEWMGWINAGNGKRKYSQKFQD
FR3-------------------------CDR3----------JH--------
RVTINRDTSASTIYMELSSLGSEDTAVYYCAREEDHAGSGSYLSMDVWGQGSTVTVSS NI-202.21D11-VK (variable light chain sequence VK; SEQ ID NO:22)
FR1--------------------CDR1-------------FR2------------CDR2---FR3--
DVVMTQSPDSLAVSLGERATINCKSSQNVLYSSNNKNYLAWYQQKPGHPPKLLIYWASTRESGVPDRF
--------------------------CDR3-----JK--------
SGSGSGTDFTLTITSLQTEDVAVYYCQQYYSSPLTFGGGTKVEIK NI-202.21D11-VK-GL (variable light chain sequence VK, corrected
according to the Germ Line Sequence; SEQ ID NO:26)
FR1--------------------CDR1-------------FR2------------CDR2---FR3--
DIVMTQSPDSLAVSLGERATINCKSSQNVLYSSNNKNYLAWYQQKPGHPPKLLIYWASTRESGVPDRF
--------------------------CDR3-----JK--------
SGSGSGTDFTLTITSLQTEDVAVYYCQQYYSSPLTFGGGTKVEIK
```

Related U.S. Application Data of application No. 14/128,497, filed as application No. PCT/US2012/043701 on Jun. 22, 2012, now Pat. No. 9,580,493.

(60) Provisional application No. 61/500,580, filed on Jun. 23, 2011.

(51) Int. Cl.
  *A61P 25/28* (2006.01)
  *A61K 39/00* (2006.01)
  *A61K 39/395* (2006.01)
  *C07K 16/18* (2006.01)
  *G01N 33/68* (2006.01)
  *A61K 47/68* (2017.01)

(52) U.S. Cl.
  CPC .... *C07K 2317/34* (2013.01); *C07K 2317/565* (2013.01); *G01N 2333/47* (2013.01); *G01N 2800/28* (2013.01); *G01N 2800/2828* (2013.01); *G01N 2800/2835* (2013.01)

(56) References Cited

U.S. PATENT DOCUMENTS

| | | |
|---|---|---|
| 6,294,171 B2 | 9/2001 | McMichael |
| 6,436,401 B1 | 8/2002 | McMichael |
| 6,703,015 B1 | 3/2004 | Solomon et al. |
| 6,710,226 B1 | 3/2004 | Schenk |
| 6,713,058 B2 | 3/2004 | McMichael |
| 6,743,427 B1 | 6/2004 | Schenk |
| 6,750,324 B1 | 6/2004 | Schenk et al. |
| 6,761,888 B1 | 7/2004 | Schenk |
| 6,787,637 B1 | 9/2004 | Schenk |
| 6,913,745 B1 | 7/2005 | Schenk |
| 7,582,733 B2 | 9/2009 | Basi et al. |
| 7,700,751 B2 | 4/2010 | Basi et al. |
| 7,727,957 B2 | 6/2010 | Schenk et al. |
| 7,763,249 B2 | 7/2010 | Sugimura et al. |
| 7,893,214 B2 | 2/2011 | Schenk |
| 7,964,192 B1 | 6/2011 | Schenk |
| 8,003,097 B2 | 8/2011 | Schroeter et al. |
| 8,034,339 B2 | 10/2011 | Schenk |
| 8,106,164 B2 | 1/2012 | Gellerfors et al. |
| 8,128,928 B2 | 3/2012 | Basi et al. |
| 8,173,127 B2 | 5/2012 | Chain |
| 8,263,558 B2 | 9/2012 | Holzman et al. |
| 8,337,848 B2 | 12/2012 | Kidd et al. |
| 8,378,061 B2 | 2/2013 | Drysdale et al. |
| 8,906,367 B2 | 12/2014 | Nitsch et al. |
| 8,940,276 B2 | 1/2015 | Weihofen et al. |
| 9,580,493 B2 | 2/2017 | Weihofen et al. |
| 9,896,504 B2 | 2/2018 | Weihofen et al. |
| 9,975,947 B2 | 5/2018 | Weihofen et al. |
| 2002/0086847 A1 | 7/2002 | Chain |
| 2004/0219146 A1 | 11/2004 | Schenk |
| 2004/0265301 A1 | 12/2004 | Schenk et al. |
| 2005/0013815 A1 | 1/2005 | Schenk |
| 2005/0048049 A1 | 3/2005 | Schenk |
| 2005/0249725 A1 | 11/2005 | Schenk et al. |
| 2005/0249727 A1 | 11/2005 | Schenk |
| 2006/0165682 A1 | 7/2006 | Basi et al. |
| 2006/0235207 A1 | 10/2006 | Tsuchiya et al. |
| 2007/0031416 A1 | 2/2007 | Shoji et al. |
| 2007/0190046 A1 | 8/2007 | DeMaattos et al. |
| 2008/0050367 A1 | 2/2008 | Basi et al. |
| 2008/0214515 A1 | 9/2008 | Ferrari et la. |
| 2008/0281082 A1 | 11/2008 | Basi et al. |
| 2008/0292625 A1 | 11/2008 | Schroeter et al. |
| 2008/0300204 A1 | 12/2008 | Federoff et al. |
| 2009/0035295 A1 | 2/2009 | Hillen et al. |
| 2009/0069268 A1 | 3/2009 | Shepard et al. |
| 2009/0069544 A1 | 3/2009 | Basi et al. |
| 2009/0191190 A1 | 7/2009 | Barghorn et al. |
| 2009/0191231 A1 | 7/2009 | Schenk et al. |
| 2009/0238831 A1 | 9/2009 | Hillen et al. |
| 2009/0246145 A1 | 10/2009 | Small |
| 2010/0120787 A1 | 5/2010 | Sutcliffe et al. |
| 2010/0202968 A1 | 8/2010 | Nitsch et al. |
| 2010/0203631 A1 | 8/2010 | Chilcote et al. |
| 2010/0209417 A1 | 8/2010 | Lee et al. |
| 2010/0209422 A1 | 8/2010 | Ravetch et al. |
| 2010/0221187 A1 | 9/2010 | Lieberburg et al. |
| 2010/0239591 A1 | 9/2010 | Kidd et al. |
| 2010/0256596 A1 | 10/2010 | Chomas |
| 2010/0279433 A1 | 11/2010 | Holzman et al. |
| 2010/0297108 A1 | 11/2010 | Henco et al. |
| 2011/0044985 A1 | 2/2011 | Rosenthal et al. |
| 2011/0044986 A1 | 2/2011 | Biere-Citron et al. |
| 2011/0052498 A1 | 3/2011 | Lannfelt et al. |
| 2011/0059092 A1 | 3/2011 | Vanmechelen et al. |
| 2011/0092434 A1 | 4/2011 | Mandler et al. |
| 2011/0135660 A1 | 6/2011 | Schenk et al. |
| 2011/0182809 A1 | 7/2011 | Nitsch et al. |
| 2011/0200609 A1 | 8/2011 | Glabe et al. |
| 2011/0212109 A1 | 9/2011 | Barghorn et al. |
| 2011/0229413 A1 | 9/2011 | Lieberburg et al. |
| 2011/0287005 A1 | 11/2011 | Hillen et al. |
| 2011/0300077 A1 | 12/2011 | Weihofen et al. |
| 2011/0306756 A1 | 12/2011 | Schenk |
| 2012/0027755 A1 | 2/2012 | Lannfelt et al. |
| 2012/0082667 A1 | 4/2012 | Yokoseki et al. |
| 2012/0156193 A1 | 6/2012 | Yokoseki et al. |
| 2012/0177664 A1 | 6/2012 | Yokoseki et al. |
| 2013/0216555 A1 | 8/2013 | Nitsch et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2014/0295465 A1 | 8/2014 | Weihofen et al. |
| 2014/0369940 A1 | 12/2014 | Weihofen et al. |
| 2015/0147343 A1 | 5/2015 | Nitsch et al. |
| 2015/0232542 A1 | 8/2015 | Weihofen et al. |
| 2016/0244515 A1 | 8/2016 | Weihofen et al. |
| 2017/0233463 A1 | 8/2017 | Weihofen et al. |
| 2018/0011112 A1 | 1/2018 | Weihofen et al. |
| 2018/0371065 A1 | 12/2018 | Weihofen et al. |

FOREIGN PATENT DOCUMENTS

| | | |
|---|---|---|
| EP | 1172376 | 1/2002 |
| EP | 1212088 | 5/2006 |
| EP | 1679080 | 7/2006 |
| EP | 1690547 | 8/2006 |
| EP | 1741783 | 1/2007 |
| EP | 1033996 | 6/2008 |
| EP | 1358213 | 11/2008 |
| EP | 1994937 | 11/2008 |
| EP | 2045267 | 4/2009 |
| EP | 2108376 | 10/2009 |
| EP | 1861422 | 2/2010 |
| EP | 2204381 | 7/2010 |
| EP | 2210901 | 7/2010 |
| EP | 1766396 | 8/2010 |
| EP | 1613347 | 9/2010 |
| EP | 1185296 | 1/2011 |
| EP | 2305282 | 4/2011 |
| EP | 2305709 | 4/2011 |
| EP | 2361629 | 8/2011 |
| EP | 2364719 | 9/2011 |
| EP | 1720909 | 11/2011 |
| JP | 2003509020 | 3/2003 |
| JP | 2005528588 | 8/2003 |
| JP | 2006265189 | 10/2006 |
| JP | 2007536895 | 12/2007 |
| JP | 2008524247 | 7/2008 |
| JP | 2009519708 | 5/2009 |
| JP | 2010532976 | 10/2010 |
| JP | 2011501655 | 1/2011 |
| JP | 2011512363 | 4/2011 |
| WO | WO1993014125 | 7/1993 |
| WO | WO1999050300 | 10/1999 |
| WO | WO2001018169 | 3/2001 |
| WO | WO2001098361 | 12/2001 |
| WO | WO2003007858 | 1/2003 |

(56) References Cited

FOREIGN PATENT DOCUMENTS

| | | |
|---|---|---|
| WO | WO2003069332 | 8/2003 |
| WO | WO2004095031 | 11/2004 |
| WO | WO2004108895 | 12/2004 |
| WO | WO2005018424 | 3/2005 |
| WO | WO2005025616 | 3/2005 |
| WO | WO2005047860 | 5/2005 |
| WO | WO2005060641 | 7/2005 |
| WO | WO2005123775 | 12/2005 |
| WO | WO2006020581 | 2/2006 |
| WO | WO2006050041 | 5/2006 |
| WO | WO2006066171 | 6/2006 |
| WO | WO2006103116 | 10/2006 |
| WO | WO2006116192 | 11/2006 |
| WO | WO2006118959 | 11/2006 |
| WO | WO2007011907 | 1/2007 |
| WO | WO2007012061 | 1/2007 |
| WO | WO2007021255 | 2/2007 |
| WO | WO2007068412 | 6/2007 |
| WO | WO2008081008 | 7/2008 |
| WO | WO2008103472 | 8/2008 |
| WO | WO2008110372 | 9/2008 |
| WO | WO2008131298 | 10/2008 |
| WO | WO2008148884 | 12/2008 |
| WO | WO2009033743 | 3/2009 |
| WO | WO2009040134 | 4/2009 |
| WO | WO2009103105 | 8/2009 |
| WO | WO2010032059 | 3/2010 |
| WO | WO2010069603 | 6/2010 |
| WO | WO2012177972 | 12/2012 |
| WO | WO2013140349 | 9/2013 |

OTHER PUBLICATIONS

Abcam, "Anti-pan Synuclein antibody (ab6176)," Abcam Inc., United States, last updated Jun. 2012, accessed at <http://abcam.com/pan-Synuclein-antibody-ab6176.html> on Jun. 27, 2012, 2 pages.
Adderson, E.A., et al., "Molecular analysis of polyreactive monoclonal antibodies from rheumatic carditis: human anti-N-acetylglucosamine/anti-myosin antibody V region genes" *J. Immounol.*, 161:2020-2031 (1998), 13 pages.
Alloul, K. et al., "Alzheimer's disease: a review of the disease, its epidemiology and economic impact" *Arch. Gerontol. Geriatr.* 27:189-221 (1998), 33 pages.
Baba, M., et al., "Aggregation of α-Synuclein in Lewy bodies of Sporadic Parkinson's Disease and Dementia with Lewy Bodies," *Am. J. Pathol.*152(4):879-884, American Society for Investigative Pathology, Untied States (1998), 6 pages.
Bard, F., et al., "Epitope and isotype specificities of antibodies to β-amyloid peptide for protection against Alzheimer's disease-like neuropatholgy" *PNAS*, 100(4):2023-2028 (2003), 6 pages.
Bard, F., et al., "Peripherally administered antibodies against amyloid β-peptide enter the central nervous system and reduce pathology in a mouse model of Alzheimer disease" *Nat. Med.*, 6:916-919 (2000), 4 pages.
Basi, G.S., et al., "Structural Correlates of Antibodies Associated with Acute Reversal of Amyloid β-related Behavioral Deficits in a Mouse Model of Alzheimer Disease" *J. Biol. Chem.*, 285(5):3417-3427 (2010), 11 pages.
BD Transduction laboratories, "Technical Data sheet: Purified Mouse Anti-α-Synuclein," BD Biosciences, United States, accessed on Jun. 27, 2012, 2 pages.
Becker, M., et al., "Stimulation of endogenous neurogenesis by anti-EFRH immunization in a transgenic mouse model of Alzheimer's disease" *PNAS* 104(5):1691-1696 (2007), 6 pages.
Bennett, M.C., et al., "The role of alpha-synuclein in neurodegenerative diseases" *Pharmacol Ther.* 105(3):311-331 (2005).
Bernasconi, N.L., et al., "Maintenance of Serological Memory by Polyclonal Activation of Human Memory B Cells" *Science* 298:2199-2202 (2002), 3 pages.

Biogen Press Release "Biogen Presents new Data from Phase 1B Study of Investigational Alzheimer's disease Treatment Aducanumab (B11B037) at Alzheimer's Association International Conference® 2015" *Businesswire* [online] Jul. 22, 2005. Retrieved from: http://www.businesswire.com/news/home/20150722005352/en/biogen-Presents-Data-Hase-1B-Study-Investigational, on Aug. 25, 25, 2015, 5 pages.
Biscaro, B., et al., "Aβ Immunotherapy Protect Morphology and Survival of Adult-Born Neurons in doubly Transgenic APP/PS1 Mice" *J. Neurosci.* 29(45):14108-14119 (2009), 12 pages.
Bohrmann, B., et al., "Gantenerumab: A Novel Human Anti-Aβ Antibody Demonstrates Sustained Cerebral Amyloid-β Binding and Elicits Cell-Mediated Removal of Human Amyloid-β" *J. Alzheimer's Dis.* 28(1):49-69 (2012), 21 pages.
Buttini, M., et al., "β-Amyloid Immunotherapy Prevents Synaptic Degeneration in a Mouse Model of Alzheimer's Disease" *J. Neurosci.* 25:9096-9101 (2005), 6 pages.
Campbell, A., "β-amyloid: friend or foe" *Med. Hypoth.* 56(3):388-391 (2001), 4 pages.
Cassett, F., et al., "A peptide mimetic of an anti-CD4 monoclonal antibody by rational design" *Biochem Biophys Res Commun.*, 307(1):198-205 (2003), 8 pages.
Chen, Y., et al., "Selection and analysis of an optimized anti-VEGF antibody: crystal structure of an affinity-matured Fab in complex with antigen" *J. Mol. Bio.* 293(4):865-881 (1999), 17 pages.
Choi, J.Y., et al., "Fine epitope mapping of monoclonal antibodies specific to human alpha-synuclein" *Neuroscience Letters* 397(1-2):8532-8538 (2006), 6 pages.
Das, P., et al., "Amyloid-β Immunication Effectively Reduces Amyloid Deposition in FcRy Knock-Out Mice" *J. Neurosci.* 23:8532-8538 (2003), 7 pages.
Dawson, T.M., et al., "Molecular pathways of neurodegeneration in parkinson's disease" *Science* 302(5646):819-822 (2003).
Demattos, R., et al., "Peripheral anti-Aβ antibody alters CNS and plasma Aβ clearance and decreases brain A burden in a mouse model of Alzheimer's disease" *PNAS* 98(15):8850-8855 (2001), 6 pages.
Department of Health and Human Services, Food and Drug Administration, Memorandum of Meeting Minutes with Biogen Idec., with cover letter and signature page by Director Russell G. Katz, dated Nov. 19, 2009; (9 pages).
Du, Y., et al., "Human anti-β-amyloid antibodies block β-amyloid fibril formation and prevent β-amyloid-induced neurotoxicity" *Brain* 126:1935-1939 (2003), 5 pages.
Dunn, G.P., et al., "The Immunobiology of Cancer Immunosurveillance and Immunoediting" *Immunity* 21:137-148 (2004), 12 pages.
Dunstan et al., "The role of brain macrophages on the clearance of amyloid plaques following the treatment of Tc2576 with B11B037" *Alzheimer's & Dementia: The Journal of the Alzheimer's Association* 7(4):S700 [online] (2001) Retrieved from the Internet: http://www.alzheimersanddementia.com/artical/S1522-5260(11)02168-6/fulltext>, 1 page.
El-Agnaf, O.M., et al., "Alpha-synuclein implicated in Parkinson's disease is present in extracellular biological fluids, including human plasma" *FASEB J.* 17(13):1945-1947 (2003), 16 pages.
El-Agnaf, O.M., et al., "Detection of oligomeric forms of alpha-synuclein protein in human plasma as a potential biomarker for Parkinson's disease" *FASEB J.* 20(3):419-425 (2006), 7 pages.
Emadi, S., et al., "Inhibiting Aggregation of α-Synuclein with Human Single Chain Antibody Fragments," Biochem. 43:2871-2878, American Chemical Society, United States (2004), 8 pages.
Emadi, S., et al., "Isolation of a human single chain antibody fragment against oligomeric α-synuclein that inhibits aggregation and prevents α-synuclein induced toxicity," *J. Mol. Biol.* 368(4):1132-1144, Academic Press, England (2007), 23 pages.
Email from Edward Stuart, CEO of neurimmune Therapeutics AG, to Leslie Coney, Biogen IDEC, dated Nov. 1, 2007, 1 page.
Email from Jan Grimm of Neurimmune, to ken Rhodes of Biogen IDEC, dated Oct. 13, 2009, 1 page.
Emmanouilidou, E., et al., "Assessment of α-Synuclein Secretion in Mouse and Human Brain Parenchyma" *PLoS ONE* 6(6):e22225 (2011), doi:10.1371/journal.pone.0022225, 9 pages.

(56) References Cited

OTHER PUBLICATIONS

Esposito, M.S., et al., "Neuronal Differentiation in the Adult Hippocampus Recapitulates Embryonic Development" *J. Neurosci.* 25(55):10074-10086 (2005), 13 pages.

European Patent Application No. 11185486, filed Oct. 17, 2011, by University of Zurich: Extended Search Report, including Search Opinion, dated Mar. 7, 2012, 11 pages.

European Patent Application No. 12802721, filed Jun. 22, 2012, by Biogen IDEC International neuroscience GmbH et al.: Extended Search Report, including Supplementary European Search Report and opinion, dated Feb. 2, 2015, 16 pages.

European Patent Application No. 12846452, filed Oct. 29, 2012, by Biogen International Neuroscience GmbH: Extended Search Report, including Supplementary European Search Report and Opinion, dated May 21, 2015, 4 pages.

European Patent Application No. 15166032, by Biogen International Neuroscience GmbH: Extended Search Report and Opinion, dated Oct. 27, 2015, 7 pages.

Ge, S., et al., "GABA regulates synaptic integration of newly generated neurons in the adult brain" *Nature*, 439(2):589-593 (2006), 10 pages.

George, J.M., "The Synucleins," *Genome Biol.* 3(I):reviews3002.1-3002.6, BioMed Central Ltd., England (2001), 6 pages.

George, S., et al., "α-Synuclein transgenic mice exhibit reduced anxiety-like behavior," *Exp. Neurol.* 210:788-792, Elsevier, Inc., United States (2008), 5 pages.

Geylis, V. and M. Steinitz "Immunotherapy of Alzheimer's disease (AD): From murine models to anti-amyloid beta (Aβ) human monoclonal antibodies" *Autoimmunity Reviews* 5:33-39 (2006), 7 pages.

Geylis, V., et al., "Human monoclonal antibodies against amyloid-beta from healthy adults" *Neurobiol of Aging* 26:597-606 (2005), 10 pages.

Giasson, B.I., et al., "Neuronal α-Synucleinopathy with Severe Movement Disorder in Mice Expressing A53T Human α-Synuclein," *Neuron* 34:521-533, Cell Press, United States (2002), 13 pages.

Giasson, B.I., et al., "A Panel of Epitope-Specific Antibodies Detects Protein domains Distributed Throughout Human α-Synuclein in Lewy bodies of Parkinson's Disease," *J. Neurosci. Res.* 59:528-533, Wiley-Liss, Inc. United States (2000), 6 pages.

Giraudon et al., "Semaphorin CD100 from Activated T Lymphocytes Induces Process Extension Collapse in Oligodendrocytes and Death of Immature Neural Cells" *J. Immunol.* 172:1246-1255 (2004), 10 pages.

Haass, C., et al., "Amyloid β-peptide is produced by cultured cells during normal metabolism" *Nature* 359:322-325 (1992), 4 pages.

Hammers-Casterman, C., et al., "Naturally occurring antibodies devoid of light chains" *Nature* 363(6428):446-448 (1993), 3 pages.

Hantman, A. and E. Perl "Molecular and Genetic Features of a Labeled Class of Spinal Substantia Gelatinose Neurons in a Transgenic Mouse" *J. Comp. Neurol.* 492:90-100 (2005), 11 pages.

Ho, N.F., et al., "In vivo imaging of adult human hippocamal neurogenesis: progress, pitfalls and promise" *Mol. Psychiatry* 18(4):404-416 (2013), 26 pages.

Hock, C., and R.M. Nitsch "Clinical Observations with AN-1792 Using TAPIR Analyses" *Neurodeg Dis.* 2:273-276 (2005), 1 page.

Hock, C., et al., "Antibodies against β-Amyloid Slow Cognitive Decline in Alzheimer's Disease" *Neuron* 38(4):547-554 (2003), 8 pages.

Hock, C., et al., "Generation of antibodies specific for β-amyloid by vaccination of patients with Alzheimer disease" *Nat. Med.* 8(11):1270-1275 (2002), 6 pages.

Holcomb, L., et al., "Accelerated Alzheimer-type phenotype in transgenic mice carrying both mutant amyloid precursor protein and presenilin 1 transgenes" *Nat. Med.* 4(1):97-100 (1998), 4 pages.

Holm, P., et al., "Functional mapping and single chain construction of the anti-cytokeratin 8 monoclonal antibody TS1" *Mol. Immunol.* 44:1075-1084 (2007), 10 pages.

Hsiao, K., et al., "Correlative Memory Deficits, Aβ Elevation, and Amyloid Plaques in Transgenic Mice" *Science* 274(5284):99-102 (1996), 4 pages.

Hyman, B.T., et al., "Autoanibodies to Amyloid-β and Alzheimer's disease" *Ann. Neurol.* 49:808-810 (2001).

International Preliminary Report on Patentability in International Application No. PCT/EP2009/009186, dated Jun, 21, 2011, 6 pages.

International Preliminary Report on Patentability in International Application No. PCT/US2012/043701, dated Dec. 23, 2013, 8 pages.

International Preliminary Report on Patentability in International Application No. PCT/US2012/062430, dated May 6, 2014, 8 pages.

International Search Report and Written Opinion dated Jan. 24, 2013, issued in International Patent Application No. PCT/US2012/62430, filed Oct. 29, 2012, by Biogen Idec International Neuroscience GmbH, 10 pages.

International Search Report and Written Opinion dated Sep. 26, 2012, Issued in International Patent Application No. PCT/US2012/043701, filed Jun. 22, 2012, by Biogen Idec International Neuroscience GmbH, 11 pages.

International Search Report and Written Opinion dated Dec. 3, 2010, for International patent Application No. PCT/EP2009/009186, European Patent Office, Netherlands, dated Mar. 12, 2010, 11 pages.

International Search Report and Written Opinion Issued in International patent Application No. PCT/IB/2009/06666, Filed Jul. 9, 2009, by university of Zurich, dated Jul. 1, 2010; ISA/European Patent Office, 16 pages.

International Search Report and Written Opinion in International Patent Application No. PCT/EP2008/000053, filed Jan. 7, 2008, by the University of Zurich, dated Jul. 9, 2009, 19 pages.

Invitrogen, "Mouse anti-α-Synuclein: For In vitro Diagnostic use," 3 pages, Invitrogen Corporation, England, last revised Aug. 2008, accessed on Jul. 2, 2012, 3 pages.

Iwai, A., et al., "Non-AB Component of Alzheimer's Disease Amyloid (NAC) Is Amyloidogenic," *Biochemistry* 34:10139-10145, American Chemical Society, United States (1995), 8 pages.

Jakes, R., et al., "Epitope mapping of LB509, monoclonal antibody directed against human α-synuclein," *Neuroscience Letters* 269:13-16, Elsevier Science Ireland Ltd., Ireland (1999), 4 pages.

Janus, C., et al., "Spatial learning in transgenic mice expressing human presenilin 1 (PS1) transgenes" *Neurobiol. Aging* 21(4):541-549 (2000), 9 pages.

Jensen, P.H., et al., "Residues in the synuclein consensus motif of the α-synuclein fragment, NAC, participate in transglutaminase-catalysed cross-linking to Alzheimer-disease amyloid BA4 peptide," *Biochem. J.* 310:91-94, Portland Press, England (1995), 4 pages.

Jin, K., et al., "vascular endothelial growth factor (VEGF) stimulates neurogenesis in vitro and in vivo" *PNAS* 99(18):11946-11950 (2002), 5 pages.

Kahle, P.J., et al., "Subcellular Localization of Wild-Type of Parkinson's Disease Associated Mutant α-Synuclein in Human and Transgenic Mouse Brain," *J. Neurosci.* 20(17):6365-6373, Society for Neuroscience, United States (2000), 9 pages.

Kahle, P.J., et al., "Selective Insolubility of α-Synuclein in Human Lewy Body Diseases is Recapitulated in a Transgenic Mouse Brain" *J. Neurosci* 20(17):6365-6373 (2001), 11 pages.

Kawarabayashi, T., et al., "Age-dependent Changes in Brain, CSF, and Plasma Amyloid β protein in the Tg2576 Transgenic Mouse Model of Alzheimer's Disease" *J. Neurosci* 21(2):372-381 (2001), 10 pages.

Knoblach, M, et al., "Intracellular Aβ and cognitive deficits precede β-amyloid deposition in transgenic arcAβ mic" *Neurobiol. Aging* 28:1297-1306 (2007), 10 pages.

Kohler, G. and C. Milstein "Continuous cultures of fused cells secreting antibody and predefined specificity" *Nature* 256:495-497 (1975), 5 pages.

Kumanogoh, A., et al.,"Requirement for the Lymphocyte Sernaphorin, CD100 in the induction of Antigen-Specific T Cells and the Maturation of Dendritic Cells" *J. Immunol.* 169:1175-1181 (2002), 8 pages.

(56) References Cited

OTHER PUBLICATIONS

Lauren, J., et al. "Cellular prion protein mediates impairment of synaptic plasticity by amyloid-β oligomers" *Nature* 457:1128-1132 (2009), 13 pages.
Lee, G.D., et al., "Stereological analysis of microvascular parameters in a double transgenic model of Alzheimer's disease" *Brain Res. Bull.* 65(4):317-322 (2005), 6 pages.
Lee, H-J., et al., "Enzyme-linked immunosorbent assays for alpha-synclein with species and multimeric state specificities" *J. Neurosci. Meth.* 199(2):249-257 (2011), 9 pages.
Lee, P.H., et al., "The plasma alpha-synuclein levels in patients with Parkinson's disease and multiple system atrophy" *J Neural Transm.* 113(10):1435-1439 (2006), 6 pages.
Lehman, D.W., et al. "Amino acid sequence of the variable region of a human μchain: Location of a possible $J_H$ segment" *Proc. Natl. Acad. Sci. USA* 77(6):3239-3243 (1980), 5 pages.
Li, Q.X., et al., "Plasma alpha-synuclein is decreased in subjects with Parkinson's disease" *Exp Neurol.* 204(2):583-588 (2007), 6 pages.
Lippa, C.F., et al., "Antibodies to α-Synuclein Detect Lewy bodies in Many Down's syndrome Brains with Alzheimer's Disease," *Ann. Neurol.* 45:353-357, American Neurological Association, United States (1999), 7 pages.
Liu, S., et al., "alpha-Synuclein produces a long-lasting increase in neurotransmitter release" *EMBO J.* 23(22):4506-4516 (2004), 11 pages.
Liu, Y., et al., "Amyloid β peptide alters intracellular vesicle trafficking and cholesterol homeostasis" *Proc. Natl. Acad. Sci. USA* 95:13266-13271 (1998), 6 pages.
Lopez-Toledano, M. and M. L. Shelanki "Neurogenic Effect of β-Amyloid Peptide in the Development of Neural Stem Cells" *J. Neurosci.* 24:5439-5444 (2004), 6 pages.
Lynch, S.M., et al., "An ScFv Intrabody Against the Non-Amyloid Component of Alpha Synuclein reduces Intracellular Aggregation and Toxicity," *J. Mol. Biol.* 377(1):136-147, Academic Press, England (2007), 17 pages.
Maccallum, R.M., et al., "Antibody-antigen interactions: contact analysis and binding site topography" *J. Mol. Biol.* 262(5):732-745 (1996), 14 pages.
Maguire-Zeiss, K.A., et al., "Identification of human alpha-synuclein specific single chain antibodies" *Biochem. Biophys. Res. Commun.*, 349(4):1198-1205 (2006), 25 pages.
Masliah, E., et al., "Dopaminergic Loss and Inclusion Body Formation in α-Synuclein Mice: Implications for Neurodegenerative Disorders" *Science* 287(5456):1265-1269 (2000), 5 pages.
Masliah, E., et al., "Effects of α-Synuclein Immunization in a Mouse Model of Parkinson's Disease," *Neuron* 46:854-868, Elsevier Inc., United States (2005), 12 pages.
Masliah, E et al., "Passive immunization reduces behavioral and neuropathological deficits in an alpha-synuclein transgenic model of Lewy body disease" *PLoS One*, 6(4):e19338 (2011), 17 pages.
Masters, C.L., et al., "Amyloid plaque core protein in Alzheimer disease and Down syndrome" *Proc. Natl. Acad. Sci. USA* 82:4245-4249 (1985), 5 pages.
Masuda, M., et al., "Inhibition of-synuclein fibril assembly by small molecules: Analysis using epitope-specific antibodies" *FEBS Lett.* 583(4):787-791 (2009), 5 pages.
Mcheyzer-Williams, M.G. and R. Ahmed "B cell memory and the long-lived plasma cell" *Curr. Opin. Immunol.* 11:172-179 (1999), 10 pages.
McLaurin, J., et al., "Therapeutically effective antibodies against amyloid-β peptide target amyloid-β residues 4-10 and inhibit cytotoxicity and fibrillogenesis" *Nat. med.* 8(11):1263-1269 (2002), 7 pages.
Miller, T.W. and Messer, A.,, "Intrabody Applications in Neurological Disorders: Progress and Future Prospects," *Molecular Therapy* 12:394-401, American Society of Gene Therapy, United States (2005), 8 pages.
Mollenhauer, B., et al., "Direct quantification of CSF alpha-synuclein by ELISA and first cross-sectional study in patients with neurodegeneration" *Exp Neural.* 213(2):315-325 (2008), 11 pages.
Mollenhauer, B., et al., "Quantification of alpha-synclein in cerebrospinal fluid as biomarker candidate: review of the literature and considerations for future studies" *Biomarkers in Medicine* 4(5):683-699 (2010), 17 pages.
Morgan, D., et al., "Aβ peptide vaccination prevents memory loss in an animal model of Alzheimers's disease" *Nature* 408:982-985 (2000), 13 pages.
Mougenot, A.L.J., et al., "Production of a monoclonal antibody, against human α-synuclein, in a subpopulation of C57BL/6J mice, presenting a deletion of the α-synuclein locus" *J. Neurosci. Meth.* 192(2):268-276 (2010), 9 pages.
Mruthinti, S., et al., "Autoimmunity in Alzheimer's disease: increased levels of circulating IgGs binding Aβ and RAGE peptides" *Neurobiol. Aging* 25:1023-1032 (2004), 10 pages.
Mueggler, T., et al., "Compromised Hemodynamic Response in Amyloid Precursor Protein Transgenic Mice" *J. Neurosci.* 22:7218-7224 (2002), 7 pages.
Muller, S., et al., "TransMabs: cell-penetrating antibodies, the next generation," *Expert Opin. Biol. Ther.* 5(2):237-241, Ashley Publications Ltd, England (2005), 5 pages.
GenBank Accession No. P37840.1, "RecName: Full=Alpha-synuclein; AltName: Full=Non-A beta component of AD amyloid; AltName: Full=non-A4 component of amyloid precursor; Short= NACP" dated Jun. 13, 2012; accessed Apr. 22, 2016 (11 pages).
GenBank Accession No. S56746, "alpha-synuclein, NAC—human (fragment)" dated Jan. 21, 2000; accessed Apr. 22, 2016 (1 page).
Neff, F., et al., "Immunotherapy and naturally occurring autoantibodies in neurodegenerative disorders," *Autoimmunity Reviews* 7:501-507, Elsevier B. V., Netherlands (2008), 7 pages.
Orgogozo, J.M., et al., "Subacute menigoencephalitis in a subset of patients with AD after Aβ42 immunization" *Neurology* 61(1):46-54 (2003), 11 pages.
Padlan, E.A., et al., "Structure of an antibody-antigen complex: Crystal structure of the HyHEL-10 Fab-lysozyme complex" *Proc. Natl. Acad. Sci. USA* 86(15):5938-5942 (1989), 5 pages.
Palop, J., et al., "Aberrant Excitatory Neuronal Activity and Compensatory Remodeling of Inhibitory Hippocampal Circuits in Mouse Models of Alzheimer's Disease" *Neuron* 55(5):697-711 (2007), 15 pages.
Papachroni, K.K., et al., "Autoantibodies to alpha-synuclein in inherited Parkinson's disease," *J. Neurochem.* 101:749-756, International Society for Neurochemistry, England (2007), 16 pages.
Pascalis, R., et al., "Grafting of "abbreviated" complementarity-determining regions containing specificity-determining residues essential for ligand contact to engineer a less immunogenic humanized monoclonal antibody" *J. Immunol.* 169(6):3076-3084 (2002), 9 pages.
Patrias, L.M., et al., "Specific antibodies to soluble alpha-synuclein conformations in intravenous immunoglobulin preparations" *Clin Exp Immunol.* 161(3): 527-535 (2010), 9 pages.
Paul, W.E. (Ed.) *Fundamental Immunology*, Third Edition. Raven Press, New York, 1993, pp. 292-295, 6 pages.
Perrin, R.J., et al., "Epitope mapping and specificity of the anti-α-synuclein monoclonal antibody Syn-1 in mouse brain and cultured cell lines" *Neurosci. Lett.* 349(2):133-135 (2003), 3 pages.
Peters, A. and I.R. Kaiserman-Abramof "The Small Pyramidal neuron of the Rat Cerebral Cortex, The Perikaryon, Dendrites and Spines" *Am. J. Anat.* 127:321-355 (1970), 35 pages.
Pfeifer, M., et al., "Cerebral Hemorrhage After Passive Anti-Aβ Immunotherapy" *Science* 298:1379 (2002), 3 pages.
Plant L.D., et al., "The production of amyloid β peptide is a critical requirement for the viability of central neurons" *J. Neurosci.* 23(13):5531-5535 (2003), 5 pages.
Plump, T., et al., "Variability of doublecortin-associate dendrite maturation in adult hippocampal neurogenesis is independent of the regulation of precursor cell proliferation" *BMC Neurosci.* 7:77 (2006), doi: 10.1186/1471-2202-7-77, 14 pages.
Priller, C., et al., "Synapse Formation and Function is Modulated by the Amyloid Precursor Protein" *J. Neurosci.* 26(27):7212-7221 (2006), 10 pages.
Qui, X-Q., et al., "Small antibody mimetics comprising two complimentary-determining regions and a framework region for tumor targeting" *Nature Biotech.* 25:921-929 (2007), 9 pages.

(56) References Cited

OTHER PUBLICATIONS

Racke, M.M., et al., "Exacerbation of Cerebral Amyloid Angiopathy-Associated Microhemorrhage in Amyloid Precursor Protein Transgenic Mic by Immunotherapy Is Dependent on Antibody Recognition of Deposited Forms of Amyloid β" J. Neurosci. 25:629-636 (2005), 8 pages.

Robert, R., et al., "Engineered antibody intervention strategies for Alzheimer's disease and related dementias by targeting amyloid and toxic oligomers," Protein Eng. Des. Sel. 22(3):199-208 Oxford University Press, England (2009), 10 pages.

Rudikoff, S., et al., "Single amino acid substitution altering antigen-binding specificity" Proc Natl Acad Sci USA 79(6):1979-83 (1982), 5 pages.

Ruszczycki, B., et al., "Sampling issues in quantitative analysis of dendritic spines morphology," BMC Bioinformatics 13:312 (2012), http:www.biomedcentral.com/1471-2105/13/213. (12 pages).

Ryu, E.K. and X. Chen "Development of Alzheimer's disease imaging agents for clinical studies" Front. Biosci. 13:777-789 (2008), 13 pages.

Schenk et al., "Amyloid-β immunotherapy for Alzheimer's disease: the end of the beginning" nat. Rev. Neurosci. 3(10):824-828 (2002), 5 pages.

Schenk et al "Immunization with amyloid-β attenuates Alzheimer-disease-like pathology in the PDAPP mouse" Nature 400:173-177 (1999), 5 pages.

Seitz, F., et al., "Isolation und charakterisierung eines physiologisch vokommenden Autoantikopers gegen humanes alpha-Synuclein," Akt Neurologie 35:S86, Georg Thieme Verlag KG, Germany (2008), 6 pages.

Serrano-Pozo, A., et al., "Neuropathological Alterations in Alzheimer Disease" Cold Spring Harb. Persepct. Med. 1:a006189 (23 pages).

Shankar, G.M., et al., "Natural oligomers of the Alzheimer amyloid-β protein induce reversible synapse loss by modulating an NMDA-type glutamate receptor-dependent signaling pathway" J. Neurosci. 27(11):2866-2875 (2007), 10 pages.

Shi, W., et al., "the Class IV Semaphorin CD100 Plays Nonredundant Roles in the Immune System: Defective B and T Cell Activation in CD100-Deficient Mice" Immunity 13:633-642 (2000), 10 pages.

Sierra, A., et al., "Adult human neurogenesis: from microscopy to magnetic resonance imaging" Front neurosci. 5, Article 47 (2011), doi: 10.3389/fnins.2011.00047 (18 pages), 18 pages.

Sigma-Aldrich, Inc., "Monoclonal Anti-α-Synuclein. Clone Syn211. Purified mouse immunoglobulin. Product No. S 5566" Product Information, updated Jan. 2003, accessed on Jun. 27, 2012 (2 pages).

Simpson, J., et al., "Antibodies to normal and Alzheimer human brain structures from non-immunised mice of various ages" FEBS Letters 217:62-64 (1987), 3 pages.

Simpson, J., et al., "Autoantibodies to Alzheimer and Normal Brain Structures from Virus-Transformed Lymphocytes" J. Neuro Immunol. 13:1-8 (1986), 4 pages.

International Search Report and Written Opinion in International Application 201200075-8, filed Jan. 7, 2008, by University of Zurich, dated Jun. 11, 2014, 13 pages.

Sorra, K.E. and K.M. Harris "Overview on the Structure, Composition, Function, Development , and Plasticity of Hippocampal Dendritic Spines" Hippocampus 10:501-511 (2000), 11 pages.

Thakker et al., "Intracerebroventricular amyloid-antibodies reduce cerebral amyloid angiopathy and asociate micro-hemorrhages in aged Tg2576 mice" Proc. Natl. Acad. Sci. USA 106(11):4501-4506 (2009), 6 pages.

Tokunda, T., et al., "Decreased alpha-synuclein in cerebrospinal fluid of aged individuals and subjects with Parkinson's disease" Biochem Biophys Res Commun. 349(1):162-166 (2006).

Traggiai, E., et al., "An efficient method to make human monoclonal antibodies from memory B cells: potent neutralization of SARS coronavirus" Nat. Med., 10:871-875 (2004), 5 pages.

Turner, P.R. et al., "Roles of amyloid precursor protein and its fragments in regulating neural activity, plasticity and memory" Prog. Neurobiol. 70(1):1-32 (2003), 32 pages.

U.S. Appl. No. 09/724,319, inventors Schenk et al., filed Nov. 27, 2012 (Abandoned, unpublished), 111 pages.

Ueda, K., et al., "Molecular cloning of cDNA encoding an unrecognized component of amyloid in Alzheimer disease," Proc. Natl. Acad. Sci. USA 90:11282-11286, national Academy of Sciences, United States (1993), 5 pages.

Vajdos, F.F., et al., "Comprehensive functional maps of the antigen-binding site of an anti-ErbB2 antibody obtained with shotgun scanning mutagenesis." J. Mol. Biol.320(2):415-428 (2002), 14 pages.

Van der Putten, H., et al., "Neuropathology in Mice Expressing Human α-Synuclein," J. Neurosci. 20(16):6021-6029, Society for Neuroscience, United States (2000), 9 pages.

Van Praag, H., et al., "Functional neurogenesis in the adult hippocampus" Nature 415:1030-1034 (2002), 5 pages.

Wang, L-P., et al., "A subpopulation of precursor cells in the mouse dentate gyms receives synaptic GABAergic input" Mol. Cell. Neurosci. 29:181-189 (2005), 9 pages.

Wang, X., et al., "Functional soluble CD100/Sema4D released from activated lymphocytes: possible role in normal and pathologic immue responses" Blood 97(11):3498-3504 (2001), 8 pages.

Wang, Y-J., et al., "Clearance of amyloid-beta in Alzheimer's disease: progress, problems and perspectives" Drug Disc. Today 11(19/20):931-938 (2006), 8 pages.

Watanabe, C., et al., Wang, Y-J., et al., "Enhanced Immune Responses in Transgenic Mice Expressing a Truncated Form of the Lymphocyte Semaphorin CD100" J. Immunol. 167(8):4321-4328 (2001), 9 pages.

Waxman, E.A. and Giasson, B.I., "Characterization of antibodies that selectively detect α-synuclein in pathological inclusions," Acta Neuropathol. 116(1):37-46, Springer-Verlag, Germany (2008), 17 pages.

Weksler, M.E., et al., "Patients with Alzheimer disease have lower levels of serum anti-amyloid peptide antibodies than healthy elderly individuals" Exper. Gerontol. 37:943-948 (2002), 8 pages.

Wilcock, D.M., et al., "Amyloid-β vaccination, But Not Nitro-Nonsteroidal Anti-Inflammatory Drug Treatment, Increases Vascular Amyloid and Microhemorrhage While Both Reduce Parenchymal Amyloid" Neuroscience 144:950-960 (2007), 21 pages.

Wilcock, D.M., et al., "Intracranially Administered Anti-Aβ Antibodies Reduce β-Amyloid Deposition by Mechanisms Both Independent of and Associated with Microglial Activation" J. Neurosci. 23(9):3745-3751 (2003), 7 pages.

Wilcock, D.M., et al., "Passive immunotherapy against Aβ in aged APP-transgenic mice reverse cognitive deficits and depletes parenchymal amyloid deposits in spit of increased vascular amyloid and microhemorrhage" J. Neuroinflammation 1:24 (2004); doi:10.1186/1742-2094/1/24 (11 pages).

Wilcock, D.M., et al., "Quantification of cerebral amyloid angiopathy and parenchymal amyloid plaques with Congo red histochemical stain" Nat. Protoc.1(3):1591-1595 (2006), 5 pages.

Woulfe, J.M., et al., "Absence of elevated anti-alpha-synuclein and anti-EBV latent membrane protein antibodies in PD" Neurology 58(9):1435-1436 (2002), 2 pages.

Wu, H., et al., "Humanization of a murine monoclonal antibody by simultaneous optimization of framework and CDR residues" J. Mol. Biol. 294(1):151-162 (1999), 12 pages.

Zhao, J., et al., "Distinct Morphological Stages of Dentate Granule Neuron maturation in the Adult Mouse Hippocampus" J. Neurosci. 26(1)3-11 (2006), 9 pages.

Zhang, L., et al., "Semi-quantitative analysis of-synuclein in subcellular pools of rat brain neurons: An immunogold electron microscopic study using a C-terminal specific monoclonal antibody," Brain Res. 12(44):40-52, Elsevier B.V., Netherlands (2008), 13 pages.

Zlokovic, B.V., "The Blood-brain Barrier in Health and Chronic Neurodegenerative Disorders" Neuron 57:178-201 (2008), 24 pages.

U.S. Appl. No. 14/592,391, Weihofen et al., filed Aug. 26, 2011, abandoned.

U.S. Appl. No. 15/865,378, Weihofen et al., filed Jan. 9, 2018.

GenBank Accession No. NP_000336.1, "alpha-synuclein isoform NACP140 [Homo sapiens]," dated Jan. 17, 2011; accessed Jan. 7, 2018, 3 pages.

Fig. 1

NI-202.21D11-VH (variable heavy chain sequence VH; SEQ ID NO:15)
FR1------------------------CDR1-FR2-------------CDR2-----------
EVQLVESGAEVKKPGASVKVSCKASGYTFTNYAMHWVRQAPGQRLEWMGWINAGNGKRKYSQKFQD
FR3-----------------------CDR3-------------JH----------------
RVTINRDTSASTIYMELSSLGSEDTAVYYCAREEDHAGSGSYLSMDVWGQGTLVTVSS NI-202.21D11-VH-GL (GL (variable heavy chain sequence VH, corrected according to the Germ Line Sequence; SEQ ID NO:20)
FR1------------------------CDR1-FR2-------------CDR2-----------
QVQLVQSGAEVKKPGASVKVSCKASGYTFTNYAMHWVRQAPGQRLEWMGWINAGNGKRKYSQKFQD
FR3-----------------------CDR3-------------JH----------------
RVTINRDTSASTIYMELSSLGSEDTAVYYCAREEDHAGSGSYLSMDVWGQGSTVTVSS NI-202.21D11-VK (variable light chain sequence VK; SEQ ID NO:22)
FR1------------CDR1-----------------FR2---------------CDR2---FR3--
DVVMTQSPDSLAVSLGERATINCKSSQNVLYSSNNKNYLAWYQQKPGHPPKLLIYWASTRESGVPDRF
------------------------CDR3------JK--------------
SGSGSGTDFTLTITSLQTEDVAVYYCQQYYSSPLTFGGGTKVEIK NI-202.21D11-VK-GL (variable light chain sequence VK, corrected according to the Germ Line Sequence; SEQ ID NO:26)
FR1------------CDR1-----------------FR2---------------CDR2---FR3--
DIVMTQSPDSLAVSLGERATINCKSSQNVLYSSNNKNYLAWYQQKPGHPPKLLIYWASTRESGVPDRF
------------------------CDR3------JK--------------
SGSGSGTDFTLTITSLQTEDVAVYYCQQYYSSPLTFGGGTKVEIK

SEQUENCE LISTING

```
<160> NUMBER OF SEQ ID NOS: 28

<210> SEQ ID NO 1
<211> LENGTH: 140
<212> TYPE: PRT
<213> ORGANISM: Homo sapiens
<220> FEATURE:
<223> OTHER INFORMATION: alpha-synuclein

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 140
<212> TYPE: PRT
<213> ORGANISM: Mus musculus
<220> FEATURE:
<223> OTHER INFORMATION: alpha-synuclein

<400> SEQUENCE: 2

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
```

```
                        20                  25                  30

Thr Lys Glu Gly Val Leu Tyr Val Gly Ser Lys Thr Lys Glu Gly Val
                35                  40                  45

Val His Gly Val Thr Thr Val Ala Glu Lys Thr Lys Glu Gln Val Thr
            50                  55                  60

Asn Val Gly Gly Ala Val Val Thr Gly Val Thr Ala Val Ala Gln Lys
65                  70                  75                  80

Thr Val Glu Gly Ala Gly Asn Ile Ala Ala Thr Gly Phe Val Lys
                85                  90                  95

Lys Asp Gln Met Gly Lys Gly Glu Glu Gly Tyr Pro Gln Glu Gly Ile
                100                 105                 110

Leu Glu Asp Met Pro Val Asp Pro Gly Ser Glu Ala Tyr Glu Met Pro
            115                 120                 125

Ser Glu Glu Gly Tyr Gln Asp Tyr Glu Pro Glu Ala
            130                 135                 140

<210> SEQ ID NO 3
<211> LENGTH: 134
<212> TYPE: PRT
<213> ORGANISM: Homo sapiens
<220> FEATURE:
<223> OTHER INFORMATION: beta-synuclein

<400> SEQUENCE: 3

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
                20                  25                  30

Thr Lys Glu Gly Val Leu Tyr Val Gly Ser Lys Thr Arg Glu Gly Val
                35                  40                  45

Val Gln Gly Val Ala Ser Val Ala Glu Lys Thr Lys Glu Gln Ala Ser
            50                  55                  60

His Leu Gly Gly Ala Val Phe Ser Gly Ala Gly Asn Ile Ala Ala Ala
65                  70                  75                  80

Thr Gly Leu Val Lys Arg Glu Glu Phe Pro Thr Asp Leu Lys Pro Glu
                85                  90                  95

Glu Val Ala Gln Glu Ala Ala Glu Glu Pro Leu Ile Glu Pro Leu Met
                100                 105                 110

Glu Pro Glu Gly Glu Ser Tyr Glu Asp Pro Pro Gln Glu Glu Tyr Gln
            115                 120                 125

Glu Tyr Glu Pro Glu Ala
    130

<210> SEQ ID NO 4
<211> LENGTH: 127
<212> TYPE: PRT
<213> ORGANISM: Homo sapiens
<220> FEATURE:
<223> OTHER INFORMATION: gamma-synuclein

<400> SEQUENCE: 4

Met Asp Val Phe Lys Lys Gly Phe Ser Ile Ala Lys Glu Gly Val Val
1               5                   10                  15

Gly Ala Val Glu Lys Thr Lys Gln Gly Val Thr Glu Ala Ala Glu Lys
                20                  25                  30

Thr Lys Glu Gly Val Met Tyr Val Gly Ala Lys Thr Lys Glu Asn Val
                35                  40                  45
```

Val Gln Ser Val Thr Ser Val Ala Glu Lys Thr Lys Glu Gln Ala Asn
    50                  55                  60

Ala Val Ser Glu Ala Val Val Ser Ser Val Asn Thr Val Ala Thr Lys
65                  70                  75                  80

Thr Val Glu Glu Ala Glu Asn Ile Ala Val Thr Ser Gly Val Val Arg
                85                  90                  95

Lys Glu Asp Leu Arg Pro Ser Ala Pro Gln Gln Gly Glu Ala Ser
                100                 105                 110

Lys Glu Lys Glu Val Ala Glu Ala Gln Ser Gly Gly Asp
            115                 120                 125

<210> SEQ ID NO 5
<211> LENGTH: 113
<212> TYPE: PRT
<213> ORGANISM: Artificial
<220> FEATURE:
<223> OTHER INFORMATION: NI-202.12F4-VHA1b (variable heavy chain
      sequence VHA1b)
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(68)
<223> OTHER INFORMATION: CDR2
<220> FEATURE:
<221> NAME/KEY: MISC_FEATURE
<222> LOCATION: (101)..(102)
<223> OTHER INFORMATION: CDR3

<400> SEQUENCE: 5

Glu Val Gln Leu Val Gln Ser Gly Gly Gly Leu Val Glu Pro Gly Gly
1               5                   10                  15

Ser Leu Arg Leu Ser Cys Ala Val Ser Gly Phe Asp Phe Glu Lys Ala
                20                  25                  30

Trp Met Ser Trp Val Arg Gln Ala Pro Gly Gln Gly Leu Gln Trp Val
            35                  40                  45

Ala Arg Ile Lys Ser Thr Ala Asp Gly Gly Thr Thr Ser Tyr Ala Ala
    50                  55                  60

Pro Val Glu Gly Arg Phe Ile Ile Ser Arg Asp Asp Ser Arg Asn Met
65                  70                  75                  80

Leu Tyr Leu Gln Met Asn Ser Leu Lys Thr Glu Asp Thr Ala Val Tyr
                85                  90                  95

Tyr Cys Thr Ser Ala His Trp Gly Gln Gly Thr Leu Val Thr Val Ser
                100                 105                 110

Ser

<210> SEQ ID NO 6
<211> LENGTH: 5
<212> TYPE: PRT
<213> ORGANISM: Artificial
<220> FEATURE:
<223> OTHER INFORMATION: NI-202.12F4-VHA1b CDR1

<400> SEQUENCE: 6

Lys Ala Trp Met Ser
1               5

<210> SEQ ID NO 7
<211> LENGTH: 19
<212> TYPE: PRT
<213> ORGANISM: Artificial

```
<220> FEATURE:
<223> OTHER INFORMATION: NI-202.12F4-VHA1b  CDR2

<400> SEQUENCE: 7

Arg Ile Lys Ser Thr Ala Asp Gly Gly Thr Thr Ser Tyr Ala Ala Pro
1               5                   10                  15

Val Glu Gly

<210> SEQ ID NO 8
<211> LENGTH: 2
<212> TYPE: PRT
<213> ORGANISM: Artificial
<220> FEATURE:
<223> OTHER INFORMATION: NI-202.12F4-VHA1b  CDR3

<400> SEQUENCE: 8

Ala His
1

<210> SEQ ID NO 9
<211> LENGTH: 113
<212> TYPE: PRT
<213> ORGANISM: Artificial
<220> FEATURE:
<223> OTHER INFORMATION: NI-202.12F4-VHA1b-GL (aligned to the Germ Line
      Sequence)

<400> SEQUENCE: 9

Glu Val Gln Leu Val Glu Ser Gly Gly Gly Leu Val Glu Pro Gly Gly
1               5                   10                  15

Ser Leu Arg Leu Ser Cys Ala Val Ser Gly Phe Asp Phe Glu Lys Ala
            20                  25                  30

Trp Met Ser Trp Val Arg Gln Ala Pro Gly Gln Gly Leu Gln Trp Val
        35                  40                  45

Ala Arg Ile Lys Ser Thr Ala Asp Gly Gly Thr Thr Ser Tyr Ala Ala
    50                  55                  60

Pro Val Glu Gly Arg Phe Ile Ile Ser Arg Asp Asp Ser Arg Asn Met
65                  70                  75                  80

Leu Tyr Leu Gln Met Asn Ser Leu Lys Thr Glu Asp Thr Ala Val Tyr
                85                  90                  95

Tyr Cys Thr Ser Ala His Trp Gly Gln Gly Thr Leu Val Thr Val Ser
            100                 105                 110

Ser

<210> SEQ ID NO 10
<211> LENGTH: 108
<212> TYPE: PRT
<213> ORGANISM: Artificial
<220> FEATURE:
<223> OTHER INFORMATION: NI-202.12F4-VLa1
<220> FEATURE:
<221> NAME/KEY: MISC_FEATURE
<222> LOCATION: (23)..(33)
<223> OTHER INFORMATION: CDR1
<220> FEATURE:
<221> NAME/KEY: MISC_FEATURE
<222> LOCATION: (49)..(55)
<223> OTHER INFORMATION: CDR2
<220> FEATURE:
<221> NAME/KEY: MISC_FEATURE
<222> LOCATION: (88)..(98)
<223> OTHER INFORMATION: CDR3

<400> SEQUENCE: 10
```

```
Gln Ser Val Leu Thr Gln Pro Pro Ser Val Ser Val Pro Gly Gln
1               5                   10                  15

Thr Ala Arg Ile Thr Cys Ser Gly Glu Ala Leu Pro Met Gln Phe Ala
                20                  25                  30

His Trp Tyr Gln Gln Arg Pro Gly Lys Ala Pro Val Ile Val Val Tyr
            35                  40                  45

Lys Asp Ser Glu Arg Pro Ser Gly Val Pro Glu Arg Phe Ser Gly Ser
        50                  55                  60

Ser Ser Gly Thr Thr Ala Thr Leu Thr Ile Thr Gly Val Gln Ala Glu
65                  70                  75                  80

Asp Glu Ala Asp Tyr Tyr Cys Gln Ser Pro Asp Ser Thr Asn Thr Tyr
                85                  90                  95

Glu Val Phe Gly Gly Gly Thr Lys Leu Thr Val Leu
                100                 105
```

<210> SEQ ID NO 11
<211> LENGTH: 11
<212> TYPE: PRT
<213> ORGANISM: Artificial
<220> FEATURE:
<223> OTHER INFORMATION: NI-202.12F4-VLa1 CDR1

<400> SEQUENCE: 11

```
Ser Gly Glu Ala Leu Pro Met Gln Phe Ala His
1               5                   10
```

<210> SEQ ID NO 12
<211> LENGTH: 7
<212> TYPE: PRT
<213> ORGANISM: Artificial
<220> FEATURE:
<223> OTHER INFORMATION: NI-202.12F4-VLa1 CDR2

<400> SEQUENCE: 12

```
Lys Asp Ser Glu Arg Pro Ser
1               5
```

<210> SEQ ID NO 13
<211> LENGTH: 11
<212> TYPE: PRT
<213> ORGANISM: Artificial
<220> FEATURE:
<223> OTHER INFORMATION: NI-202.12F4-VLa1 CDR3

<400> SEQUENCE: 13

```
Gln Ser Pro Asp Ser Thr Asn Thr Tyr Glu Val
1               5                   10
```

<210> SEQ ID NO 14
<211> LENGTH: 108
<212> TYPE: PRT
<213> ORGANISM: Artificial
<220> FEATURE:
<223> OTHER INFORMATION: NI-202.12F4-VLa1-GL (aligned to the Germ Line
      Sequence)

<400> SEQUENCE: 14

```
Ser Tyr Glu Leu Thr Gln Pro Pro Ser Val Ser Val Pro Gly Gln
1               5                   10                  15

Thr Ala Arg Ile Thr Cys Ser Gly Glu Ala Leu Pro Met Gln Phe Ala
                20                  25                  30

His Trp Tyr Gln Gln Arg Pro Gly Lys Ala Pro Val Ile Val Val Tyr
            35                  40                  45
```

-continued

Lys Asp Ser Glu Arg Pro Ser Gly Val Pro Glu Arg Phe Ser Gly Ser
            50                  55                  60

Ser Ser Gly Thr Thr Ala Thr Leu Thr Ile Thr Gly Val Gln Ala Glu
65                  70                  75                  80

Asp Glu Ala Asp Tyr Tyr Cys Gln Ser Pro Asp Ser Thr Asn Thr Tyr
                85                  90                  95

Glu Val Phe Gly Gly Gly Thr Lys Leu Thr Val Leu
            100                 105

<210> SEQ ID NO 15
<211> LENGTH: 124
<212> TYPE: PRT
<213> ORGANISM: Artificial
<220> FEATURE:
<223> OTHER INFORMATION: NI-202.21D11-VH
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(113)
<223> OTHER INFORMATION: CDR3

<400> SEQUENCE: 15

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Lys Arg Lys Tyr Ser Gln Lys Phe
50                  55                  60

Gln Asp Arg Val Thr Ile Asn Arg Asp Thr Ser Ala Ser Thr Ile Tyr
65                  70                  75                  80

Met Glu Leu Ser Ser Leu Gly Ser Glu Asp Thr Ala Val Tyr Tyr Cys
                85                  90                  95

Ala Arg Glu Glu Asp His Ala Gly Ser Gly Ser Tyr Leu Ser Met Asp
            100                 105                 110

Val Trp Gly Gln Gly Thr Leu Val Thr Val Ser Ser
        115                 120

<210> SEQ ID NO 16
<211> LENGTH: 5
<212> TYPE: PRT
<213> ORGANISM: Artificial
<220> FEATURE:
<223> OTHER INFORMATION: NI-202.21D11-VH  CDR1

<400> SEQUENCE: 16

Asn Tyr Ala Met His
1               5

<210> SEQ ID NO 17
<211> LENGTH: 17
<212> TYPE: PRT
<213> ORGANISM: Artificial
<220> FEATURE:
<223> OTHER INFORMATION: NI-202.21D11-VH  CDR2

-continued

```
<400> SEQUENCE: 17

Trp Ile Asn Ala Gly Asn Gly Lys Arg Lys Tyr Ser Gln Lys Phe Gln
1               5                   10                  15

Asp

<210> SEQ ID NO 18
<211> LENGTH: 15
<212> TYPE: PRT
<213> ORGANISM: Artificial
<220> FEATURE:
<223> OTHER INFORMATION: NI-202.21D11-VH  CDR3

<400> SEQUENCE: 18

Glu Glu Asp His Ala Gly Ser Gly Ser Tyr Leu Ser Met Asp Val
1               5                   10                  15

<210> SEQ ID NO 19
<211> LENGTH: 372
<212> TYPE: DNA
<213> ORGANISM: Artificial
<220> FEATURE:
<223> OTHER INFORMATION: NI-202.21D11-VH

<400> SEQUENCE: 19
gaggtgcagc tggtggagtc tgggctgag gtgaagaagc cggggcctc agtgaaggtt      60 tcctgcaagg cttctggata caccttcact aactatgcta tgcattgggt gcgccaggcc    120
cccggacaaa ggcttgagtg gatgggatgg atcaacgctg gcaatggtaa agaaaatat    180 tcacagaagt tccaggacag agtcaccatt aacagggaca catccgcgag cacaatctac    240
atggagctga gcagcctggg atctgaagac acggctgtat attactgtgc gagagaggag    300
gatcacgctg gttcggggag ttacctcagt atggacgtct ggggccaagg aaccctggtc    360
accgtctcct cg                                                        372

<210> SEQ ID NO 20
<211> LENGTH: 124
<212> TYPE: PRT
<213> ORGANISM: Artificial
<220> FEATURE:
<223> OTHER INFORMATION: NI-202.21D11-VH-GL (corrected according to the
      Germ Line Sequence)

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Lys Arg Lys Tyr Ser Gln Lys Phe
    50                  55                  60

Gln Asp Arg Val Thr Ile Asn Arg Asp Thr Ser Ala Ser Thr Ile Tyr
65                  70                  75                  80

Met Glu Leu Ser Ser Leu Gly Ser Glu Asp Thr Ala Val Tyr Tyr Cys
                85                  90                  95

Ala Arg Glu Glu Asp His Ala Gly Ser Gly Ser Tyr Leu Ser Met Asp
            100                 105                 110

Val Trp Gly Gln Gly Ser Thr Val Thr Val Ser Ser
        115                 120
```

<210> SEQ ID NO 21
<211> LENGTH: 372
<212> TYPE: DNA
<213> ORGANISM: Artificial
<220> FEATURE:
<223> OTHER INFORMATION: NI-202.21D11-VH-GL

<400> SEQUENCE: 21

```
caggtgcagc tggtgcagtc tggggctgag gtgaagaagc ccggggcctc agtgaaggtt    60
tcctgcaagg cttctggata caccttcact aactatgcta tgcattgggt gcgccaggcc   120
cccggacaaa ggcttgagtg gatgggatgg atcaacgctg caatggtaa gagaaaatat    180
tcacagaagt tccaggacag agtcaccatt aacagggaca catccgcgag cacaatctac   240
atggagctga gcagcctggg atctgaagac acggctgtat attactgtgc gagagaggag   300
gatcacgctg gttcggggag ttacctcagt atggacgtct ggggccaagg aagcacggtc   360
accgtctcct cg                                                       372
```

<210> SEQ ID NO 22
<211> LENGTH: 113
<212> TYPE: PRT
<213> ORGANISM: Artificial
<220> FEATURE:
<223> OTHER INFORMATION: NI-202.21D11-VK
<220> FEATURE:
<221> NAME/KEY: MISC_FEATURE
<222> LOCATION: (26)..(40)
<223> OTHER INFORMATION: CDR1
<220> FEATURE:
<221> NAME/KEY: MISC_FEATURE
<222> LOCATION: (56)..(63)
<223> OTHER INFORMATION: CDR2
<220> FEATURE:
<221> NAME/KEY: MISC_FEATURE
<222> LOCATION: (95)..(103)
<223> OTHER INFORMATION: CDR3

<400> SEQUENCE: 22

```
Asp Val Val Met Thr Gln Ser Pro Asp Ser Leu Ala Val Ser Leu Gly
 1               5                  10                  15

Glu Arg Ala Thr Ile Asn Cys Lys Ser Ser Gln Asn Val Leu Tyr Ser
             20                  25                  30

Ser Asn Asn Lys Asn Tyr Leu Ala Trp Tyr Gln Gln Lys Pro Gly His
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                 70                  75                  80

Ile Thr Ser Leu Gln Thr Glu Asp Val Ala Val Tyr Tyr Cys Gln Gln
             85                  90                  95

Tyr Tyr Ser Ser Pro Leu Thr Phe Gly Gly Gly Thr Lys Val Glu Ile
            100                 105                 110

Lys
```

<210> SEQ ID NO 23
<211> LENGTH: 17
<212> TYPE: PRT
<213> ORGANISM: Artificial
<220> FEATURE:
<223> OTHER INFORMATION: NI-202.21D11-VK CDR1

<400> SEQUENCE: 23

Lys Ser Ser Gln Asn Val Leu Tyr Ser Ser Asn Asn Lys Asn Tyr Leu
1               5                   10                  15

Ala

<210> SEQ ID NO 24
<211> LENGTH: 7
<212> TYPE: PRT
<213> ORGANISM: Artificial
<220> FEATURE:
<223> OTHER INFORMATION: NI-202.21D11-VK  CDR2

<400> SEQUENCE: 24

Trp Ala Ser Thr Arg Glu Ser
1               5

<210> SEQ ID NO 25
<211> LENGTH: 9
<212> TYPE: PRT
<213> ORGANISM: Artificial
<220> FEATURE:
<223> OTHER INFORMATION: NI-202.21D11-VK  CDR3

<400> SEQUENCE: 25

Gln Gln Tyr Tyr Ser Ser Pro Leu Thr
1               5

<210> SEQ ID NO 26
<211> LENGTH: 113
<212> TYPE: PRT
<213> ORGANISM: Artificial
<220> FEATURE:
<223> OTHER INFORMATION: NI-202.21D11-VK-GL (corrected according to the
      Germ Line Sequence)

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Val Leu Tyr Ser
                20                  25                  30

Ser Asn Asn Lys Asn Tyr Leu Ala Trp Tyr Gln Lys Pro Gly His
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Thr Ser Leu Gln Thr Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys

<210> SEQ ID NO 27
<211> LENGTH: 339
<212> TYPE: DNA
<213> ORGANISM: Artificial
<220> FEATURE:
<223> OTHER INFORMATION: NI-202.21D11-VK-GL

<400> SEQUENCE: 27
gatattgtga tgactcagtc tccagactcc ctggctgtgt ctctgggcga gagggccacc      60
atcaactgca agtccagcca gaatgttta tacagctcca acaataagaa ctacttagct     120

```
tggtaccagc agaaaccagg acatcctcct aagttgctca tttactgggc atctacccgg    180
gaatccgggg tccctgaccg attcagtggc agcgggtctg ggacagattt cactctcacc    240
atcaccagct tgcagactga agatgtggcg gtctattact gtcagcagta ttatagtagt    300
cctctcactt tcggcggagg gaccaaggtg gagatcaaa                           339

<210> SEQ ID NO 28
<211> LENGTH: 339
<212> TYPE: DNA
<213> ORGANISM: Artificial
<220> FEATURE:
<223> OTHER INFORMATION: NI-202.21D11-VK

<400> SEQUENCE: 28
gatgttgtga tgactcagtc tccagactcc ctggctgtgt ctctgggcga gagggccacc     60
atcaactgca agtccagcca gaatgtttta tacagctcca acaataagaa ctacttagct    120
tggtaccagc agaaaccagg acatcctcct aagttgctca tttactgggc atctacccgg    180
gaatccgggg tccctgaccg attcagtggc agcgggtctg ggacagattt cactctcacc    240
atcaccagct tgcagactga agatgtggcg gtctattact gtcagcagta ttatagtagt    300
cctctcactt tcggcggagg gaccaaggtg gagatcaaa                           339
```

ANTI-ALPHA SYNUCLEIN BINDING MOLECULES

CROSS-REFERENCE TO RELATED APPLICATIONS

This application is a divisional of U.S. application Ser. No. 15/410,128, filed on Jan. 19, 2017, which is a divisional of U.S. application Ser. No. 14/128,497, filed on Aug. 29, 2014, now U.S. Pat. No. 9,580,493, which is the National Stage of International Application No. PCT/US2012/043701, filed on Jun. 22, 2012, which claims the benefit of priority U.S. Application No. 61/500,580, filed on Jun. 23, 2011. The disclosure of the prior applications is incorporated herein by reference.

The content of the electronically submitted sequence listing in ASCII text file (Name: sequencelisting_ascii.txt; Size: 23 KB; and Date of Creation: Jun. 23, 2011) filed with the application is incorporated herein by reference in its entirety.

BACKGROUND OF THE INVENTION

The present invention generally relates to novel α-synuclein-specific binding molecules, particularly human antibodies as well as fragments, derivatives and variants thereof that recognize α-synuclein and aggregated forms of α-synuclein, respectively. In addition, the present invention relates to pharmaceutical and diagnostic compositions comprising such binding molecules, antibodies and mimics thereof valuable both as a diagnostic tool to identify toxic species of α-synuclein in plasma and CSF and also in passive vaccination strategies for treating disorders related to aggregates of α-synuclein such as Parkinson's disease (PD), dementia with Lewy bodies (DLB) and Lewy body variant of Alzheimer's disease (AD) and other synucleinopathic diseases.

Protein misfolding and aggregation are pathological aspects of numerous neurodegenerative diseases. Aggregates of α-synuclein are major components of the Lewy bodies and Lewy neurites associated with Parkinson's disease (PD). A natively unfolded protein, α-synuclein can adopt different aggregated morphologies, including oligomers, protofibrils and fibrils. The small oligomeric aggregates have been shown to be particularly toxic.

Naturally occurring autoantibodies against α-synuclein have been detected in healthy persons and altered levels in patients were associated with particular neurodegenerative disorders; see for review Neff et al., Autoimmun. Rev. 7 (2008), 501-507. Thus, naturally occurring antibodies in patients suffering from Parkinson's disease, either spontaneously or upon vaccination, in particular in healthy patients can serve a protective role with respect to α-synuclein aggregation; see, e.g., Woulfe et al., Neurology 58 (2002), 1435-1436 and Papachroni et al., J. Neurochem. 101 (2007), 749-756. Hitherto, the therapeutic significance of autoantibodies had been difficult to assess. This is mostly due to the lack of straight-forward experimental approaches for their isolation and subsequent characterization in vitro.

Recently, oligomeric species of α-synuclein have been reported extracellularly in plasma and CSF (El-Agnaf et al., FASEB J. 20 (2006), 419-425) and immunization studies in mouse models of PD show that extracellular mouse monoclonal antibodies against α-synuclein can reduce accumulation of intracellular α-synuclein aggregates (Masliah et al., Neuron, 46 (2005), 857-868) supporting the idea that antibodies that neutralize the neurotoxic aggregates without interfering with beneficial functions of monomeric α-synuclein can be useful therapeutics. However, the therapeutic utility of murine based antibodies in human is hampered by the human anti-mouse antibody (HAMA) response in view of their non-human origin.

Emadi et al. in J. Mol. Biol. 368 (2007), 1132-1144, describe the isolation of single chain antibody fragments (scFvs) from a phage displayed antibody library based on human sequences against α-synuclein, which bind only to an oligomeric form of α-synuclein and inhibit both aggregation and toxicity of α-synuclein in vitro. However, although the generation of scFvs from phage display is rather simple, this technique has severe drawbacks since the antibodies so produced bear the risk of undesired crossreactivity against self-antigens and lack the characteristics of evolutionary optimized natural human antibodies produced by the human immune system. Furthermore, such antibodies may not be specific enough because of cross-reactivity with other proteins and/or with the target protein in context with normal physiological environment and function. In case of Parkinson's disease, for example, antibodies that also cross-react with physiological derivatives of α-synuclein bear the potential to cause side effects related to the normal functions of the physiologic target structures. In this respect, an undesired autoimmune disease would downrightly be induced—a hardly calculable risk also in the conceptual design of active immunization experiments employing protein structures that, in variant form, also occur physiologically.

More recently, Seitz et al. (81. Kongress der Deutschen Gesellschaft für Neurologie mit Fortbildungsakademie Hamburg 10.-13.09.2008), reported on the isolation of anti-α-synuclein polyclonal autoantibody from different immunoglobulin solutions and samples of single blood donors through affinity chromatography. However, besides the fact that this approach provides mere limited amounts of the desired antibody, polyclonal antibodies are of only limited use for therapeutic application, for example because of their heterogeneity and the risk of being contaminated with other α-synuclein associated molecules which have undesired side effects. Likewise, the diagnostic value of polyclonal antibodies is reduced since the variability of the composition of the antibodies will influence the overall specificity and reactivity. This is all the more true for antibodies against proteins subject of aggregation and deposition due to misfolding.

Thus, there is a need to overcome the above-described limitations and to provide a therapeutic and diagnostic human antibody against α-synuclein.

SUMMARY OF THE INVENTION

In one embodiment, the present invention provides an isolated binding molecule which specifically binds to an epitope within amino acids 4 to 15 of human α-synuclein (SEQ ID NO:1). In certain aspects the binding molecule competitively inhibits the binding of reference monoclonal antibody NI-202.12F4 to α-synuclein. A binding molecule of the invention can be an antibody, or an antigen-binding fragment thereof. In particular embodiments the binding molecule is not human monoclonal antibody NI-202.12F4, or an antigen-binding fragment, variant, or derivative thereof.

Another embodiment provides an isolated binding molecule which specifically binds to an epitope within amino acids 113 to 123 or within amino acids 117 to 123 of α-synuclein (SEQ ID NO:1). In certain aspects the binding molecule specifically binds to the same human α-synuclein epitope as the reference monoclonal antibody NI-202.21D11, or competitively inhibits the binding reference monoclonal antibody NI-202.21D11 to human α-synuclein. A binding molecule of the invention can be an antibody, or an antigen-binding fragment thereof. A particular binding molecule of the invention is the human monoclonal antibody NI-202.21D11, or an antigen-binding fragment, variant, or derivative thereof.

The invention further provides an isolated antibody or antigen binding fragment thereof that specifically binds to human α-synuclein, comprising an immunoglobulin heavy chain variable region (VH) and an immunoglobulin light chain variable region (VL), where the VH comprises a polypeptide sequence at least 90%, or 100% identical to SEQ ID NO:15 or SEQ ID NO:20. Also provided is an isolated antibody or antigen binding fragment thereof that specifically binds to human α-synuclein, comprising a VH and a VL, where the VL comprises a polypeptide sequence at least 90%, or 100% identical to SEQ ID NO:22 or SEQ ID NO:26. Similarly, the invention provides an isolated antibody or antigen binding fragment thereof that specifically binds to human α-synuclein, comprising a VH and a VL where the VH and VL comprise, respectively, polypeptide sequences at least 90%, or 100% identical to the reference polypeptides SEQ ID NO:15 and SEQ ID NO:22, SEQ ID NO:15 and SEQ ID NO:26, SEQ ID NO:20 and SEQ ID NO:22, or SEQ ID NO:20 and SEQ ID NO:26.

Further provided are isolated polypeptides, including an isolated polypeptide comprising a VH, where the CDR1 region of the VH is identical, or identical except for less than 3 conservative amino acid substitutions, to reference heavy chain CDR1 sequence SEQ ID NO:16, an isolated polypeptide comprising a VH, where the CDR2 region of the VH is identical, or identical except for less than 5 conservative amino acid substitutions, to reference heavy chain CDR2 sequence SEQ ID NO:17, an isolated polypeptide comprising a VH, where the CDR3 region of the VH is identical, or identical except for less than 5 conservative amino acid substitutions, to reference heavy chain CDR3 sequence SEQ ID NO:18, an isolated polypeptide comprising a VL, where the CDR1 region of the VL is identical, or identical except for less than 5 conservative amino acid substitutions, to reference light chain CDR1 sequence SEQ ID NO:23, an isolated polypeptide comprising a VL, where the CDR2 region of the VL is identical, or identical except for less than 3 conservative amino acid substitutions, to reference heavy chain CDR2 sequence SEQ ID NO:24, and an isolated polypeptide comprising a VL, where the CDR3 region of the VL is identical, or identical except for less than 3 conservative amino acid substitutions, to reference heavy chain CDR3 sequence SEQ ID NO:25. In each of the above stated polypeptides, an antibody or antigen-binding fragment thereof comprising the polypeptide specifically binds to human α-synuclein.

In certain embodiments the invention the isolated antibody or fragment thereof preferentially binds to a non-linear conformational epitope of human α-synuclein. In other embodiments the isolated antibody or fragment thereof preferentially binds human α-synuclein in the oligomeric or aggregated form. In further embodiments the isolated antibody or fragment thereof does not specifically bind to human β-synuclein or human γ-synuclein, and/or does not specifically bind to murine α-synuclein.

Also provided is a composition comprising an antibody or fragment thereof as described above, and a carrier. The composition may be a therapeutic or a diagnostic composition.

Further provide are one or more isolated polynucleotides encoding a polypeptide or binding molecule as described herein, and vectors and host cells for expressing such binding molecules.

It is a particular object of the present invention to provide methods for treating or preventing a synucleinopathic disease such as, but not limited to Parkinson's disease (PD), dementia with Lewy bodies (DLB), and multiple systems atrophy (MSA). The methods comprise administering an effective concentration of anti-human α-synuclein binding molecule, e.g., an antibody or antigen binding fragment, variant, or derivative to the subject where the antibody targets α-synuclein.

It is also an object of the invention to provide a method of diagnosing a synucleinopathic disease in a subject, comprising assessing the level, localization, conformation or a combination thereof of α-synuclein in a subject to be diagnosed with an antibody or fragment thereof of the invention and comparing the level, localization, conformation or combination thereof of α-synuclein in the subject to one or more reference standards derived from one or more control samples, where a difference or similarity between the level, localization, conformation or combination thereof of α-synuclein in the subject and the reference standard indicates whether the subject has a synucleinopathic disease.

Diagnostic methods of the invention can be through in vitro assay of patient samples, or by in vivo imaging techniques.

Further embodiments of the present invention will be apparent from the description and Examples that follow.

BRIEF DESCRIPTION OF THE DRAWINGS

FIG. 1 Amino acid and nucleotide sequences of the variable region, i.e. heavy chain and kappa light chains of human antibody NI-202.21D11. Framework (FR) and complementarity determining regions (CDRs) are indicated with the CDRs being underlined. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see e.g., Vbase (vbase.mrc-cpe.cam.ac.uk) hosted by the MRC Centre for Protein Engineering (Cambridge, UK). Those amino acids, which are considered to potentially deviate from the consensus germ line sequence and thus could be due to the PCR primer, are indicated in bold.

DETAILED DESCRIPTION OF THE INVENTION

I. Definitions

Figure 2:
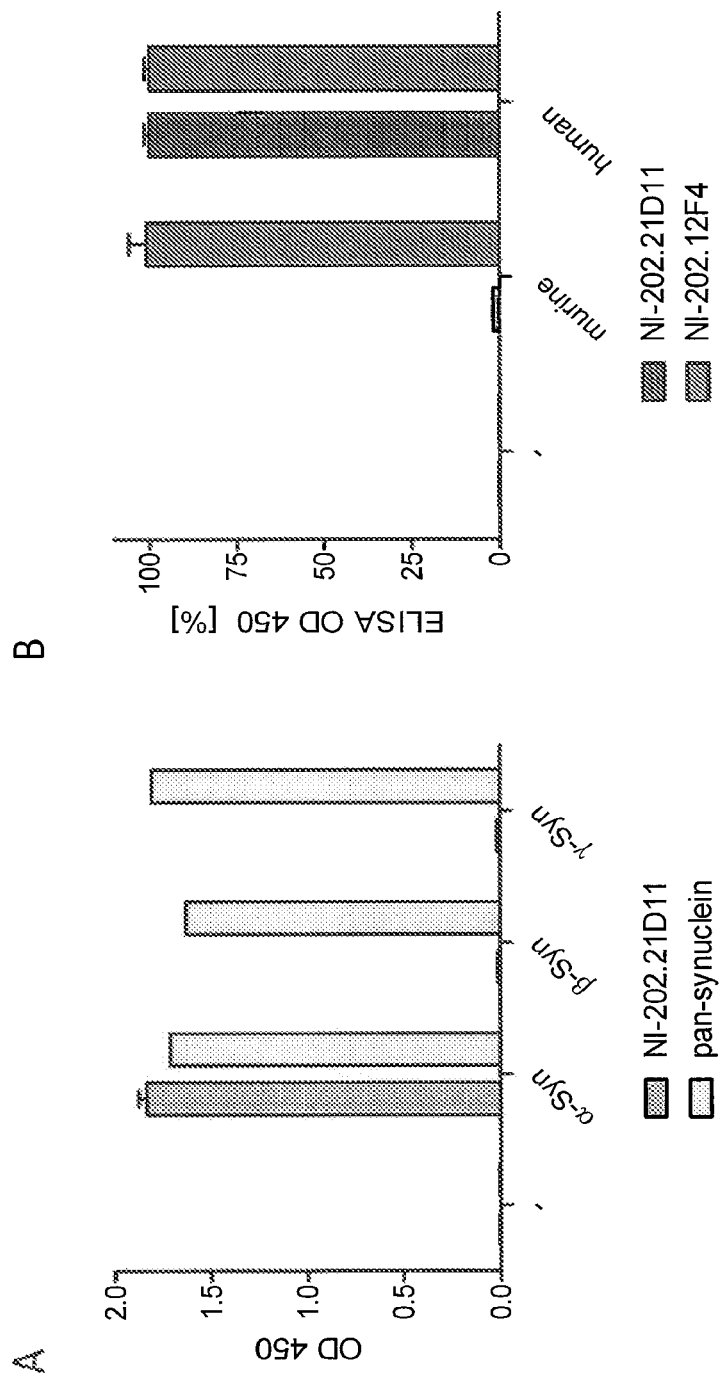
FIG. 2 Recombinant human NI-202.21D11 selectively binds human α-synuclein over β-, γ-synuclein and murine α-synuclein in a direct ELISA. Recombinant human α-, β-, γ-synuclein and recombinant human and murine His-tagged α-synuclein were coated onto ELISA plates at equal concentration (2 µg/ml). Plates were then probed with recombinant human NI-202.21D11, human NI-202.12F4 and with a pan-synuclein antibody. (A) Recombinant NI-202.21D11 selectively binds α-synuclein whereas pan-synuclein antibody binds to all three synuclein proteins confirming equal coating of recombinant proteins. (B) Recombinant NI-202.21D11 is selective for human vs murine α-synuclein. On the other hand NI-202.12F4 binds to both human and murine α-synuclein in a direct ELISA.

Synucleinopathic diseases or synucleinopathies are a diverse group of neurodegenerative disorders that share a common pathologic lesion composed of aggregates of insoluble α-synuclein protein in selectively vulnerable populations of neurons and glia. These disorders include Parkinson's disease (PD), Parkinson's Disease Dementia (PDD), dementia with Lewy bodies (DLB), juvenile-onset generalized neuroaxonal dystrophy (Hallervorden-Spatz disease), pure autonomic failure (PAF), multiple system atrophy (MSA) and neurodegeneration with brain iron accumulation type-1 (NBIA-I). Clinically, they are characterized by a chronic and progressive decline in motor, cognitive, behavioral, and autonomic functions, depending on the distribution of the lesions.

Parkinson's disease is an age-dependent neurodegenerative disease with unknown etiology. It is believed that sporadic Parkinson's disease results from a combination of genetic vulnerability and environmental insults. It is further believed that Parkinson's disease (PD) while triggered by disparate mechanisms follows a shared pathophysiologic pathway. One shared node is the involvement of α-synuclein. Linkage of this protein with Parkinson's disease pathogenesis has been established by the identification of both point mutations and triplication of the gene in familial cases, the localization of α-synuclein to Lewy bodies, one of the hallmark pathological features of Parkinson's disease, and the correlation of α-synuclein expression and disease pathology in neurotoxic models of Parkinson's disease. Further evidence indicates that particular forms of α-synuclein (e.g., misfolded and α-synuclein bonded dopamine) are involved in sporadic disease.

Synucleins are small, soluble proteins expressed primarily in neural tissue and in certain tumors. The family includes three known proteins: α-synuclein, β-synuclein, and γ-synuclein. All synucleins have in common a highly conserved α-helical lipid-binding motif with similarity to the class-A2 lipid-binding domains of the exchangeable apolipoproteins. Synuclein family members are not found outside vertebrates, although they have some conserved structural similarity with plant 'late-embryo-abundant' proteins. The α- and β-synuclein proteins are found primarily in brain tissue, where they are seen mainly in presynaptic terminals. The γ-synuclein protein is found primarily in the peripheral nervous system and retina, but its expression in breast tumors is a marker for tumor progression. Normal cellular functions have not been determined for any of the synuclein proteins, although some data suggest a role in the regulation of membrane stability and/or turnover. Mutations in α-synuclein are associated with rare familial cases of early-onset Parkinson's disease, and the protein accumulates abnormally in Parkinson's disease, Alzheimer's disease, and several other neurodegenerative illnesses. For review see, e.g., George, Genome Biol. 3 (2002), reviews3002.1-reviews3002.6 published online Dec. 20, 2001, in which Table 1 catalogs the unique members of the synuclein family that are currently listed in GenBank, the disclosure content of which is incorporated herein by reference.

α-synuclein was originally identified in human brains as the precursor protein of the non-β-amyloid component of (NAC) of Alzheimer's disease (AD) plaques; see, e.g., Ueda et al, Proc. Natl. Acad. Sci. U.S.A. 90 (1993), 1282-1286. α-synuclein, also termed the precursor of the non-A3 component of AD amyloid (NACP), is a protein of 140 amino acids. α-synuclein exists in its native form as a random coil; however, changes in pH, molecular crowding, heavy metal content, and dopamine levels all affect protein conformation. Changes in conformation to oligomeric, proto-fibrillar, fibrillar, and aggregate moieties are thought to regulate protein toxicity. Increasing evidence indicates that dopamine-adducted α-synuclein has a faster time course to fibril formation compared to non-adducted protein. Furthermore, dopamine in the background of α-synuclein overexpression is toxic.

In this specification, the terms "α-synuclein", "alpha-synuclein", "α-synuclein" and "aSyn" are used interchangeable to specifically refer to the native monomer form of α-synuclein. The term "α-synuclein" is also used to generally identify other conformers of α-synuclein, for example, α-synuclein bonded to dopamine-quinone (DAQ) and oligomers or aggregates of α-synuclein. The term "α-synuclein" is also used to refer collectively to all types and forms of α-synuclein. The protein sequence for human α-synuclein (SEQ ID NO: 1)
MDVFMKGLSKAKEGVVAAAEKTKQGVAEAAGKTKEGVLYVGSKTKEG

VVHGVATVAEKTKEQVTNVGGAVVTGVTAVAQKTVEGAGSIAAATGF

VKKDQLGKNEEGAPQEGILEDMPVDPDNEAYEMPSEEGYQDYEPEA.

The amino acid sequence of α-synuclein can be retrieved from the literature and pertinent databases; see, e.g., Ueda et al., ibid.; GenBank swissprot: locus SYUA_HUMAN, accession number P37840. The non-A3 component of AD amyloid (NAC) is derived from α-synuclein. NAC, a highly hydrophobic domain within α-synuclein, is a peptide consisting of at least 28 amino acids residues (residues 60-87) and optionally 35 amino acid residues (residues 61-95). NAC displays a tendency to form a beta-sheet structure (Iwai, et al., Biochemistry, 34 (1995) 10139-10145). The amino acid sequences of NAC are described in Jensen et al., Biochem. J. 310 (1995), 91-94; GenBank accession number S56746 and Ueda et al., PNAS USA 90 (1993), 1282-11286.

Disaggregated α-synuclein or fragments thereof, including NAC, means monomeric peptide units. Disaggregated α-synuclein or fragments thereof are generally soluble, and are capable of self-aggregating to form soluble oligomers. Oligomers of α-synuclein and fragments thereof are usually soluble and exist predominantly as α-helices. Monomeric α-synuclein can be prepared in vitro by dissolving lyophilized peptide in neat DMSO with sonication. The resulting solution is centrifuged to remove any insoluble particulates. Aggregated α-synuclein or fragments thereof, including NAC, means oligomers of α-synuclein or fragments thereof which have associate into insoluble β-sheet assemblies. Aggregated α-synuclein or fragments thereof, including NAC, means also means fibrillar polymers. Fibrils are usually insoluble. Some antibodies bind either soluble α-synuclein or fragments thereof or aggregated α-synuclein or fragments thereof. Some antibodies bind to oligomers of α-synuclein more strongly than to monomeric forms or fibrillar forms. Some antibodies bind both soluble and aggregated α-synuclein or fragments thereof, and optionally oligomeric forms as well.

The human anti-α-synuclein antibodies disclosed herein specifically bind α-synuclein and epitopes thereof and to various conformations of α-synuclein and epitopes thereof. For example, disclosed herein are antibodies that specifically bind α-synuclein, α-synuclein in its native monomer form, full-length and truncated α-synuclein and α-synuclein aggregates. As used herein, reference to an antibody that "specifically binds", "selectively binds", or "preferentially binds" α-synuclein refers to an antibody that does not bind other unrelated proteins. In one example, an α-synuclein antibody disclosed herein can bind α-synuclein or an epitope thereof and show no binding above about 1.5 times background for other proteins. An antibody that "specifically binds" or "selectively binds" α-synuclein conformer refers to an antibody that does not bind all conformations of α-synuclein, i.e., does not bind at least one other α-synuclein conformer. For example, disclosed herein are antibodies that can distinguish among monomeric and aggregated forms of α-synuclein, human and mouse α-synuclein; full-length α-synuclein and truncated forms as well as human α-synuclein versus β- and γ-synuclein. Since the human anti-α-synuclein antibodies of the present invention have been isolated from a pool of elderly subjects with no signs of Parkinsonism and exhibiting an α-synuclein-specific immune response the anti-α-synuclein antibodies of the present invention are also referred to as "human autoantibodies" in order to emphasize that those antibodies were indeed expressed by the subjects and have not been isolated from, for example a human immunoglobulin expressing phage library, which hitherto represented one common method for trying to provide human-like antibodies.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It an be generated in any manner, including by chemical synthesis.

A polypeptide of the invention can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions or additions. Derivatives of α-synuclein specific binding molecules, e.g., antibodies and antibody polypeptides of the present invention, are polypeptides which have been altered so as to exhibit additional features not found on the native polypeptide. Examples include fusion proteins. Variant polypeptides are also referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or comprise two or more coding regions, e.g., a single vector can separately encode an immunoglobulin heavy chain variable region and an immunoglobulin light chain variable region. In addition, a vector, polynucleotide, or nucleic acid of the invention can encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention can be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse ß-glucuronidase.

Unless stated otherwise, the terms "disorder" and "disease" are used interchangeably herein.

A "binding molecule" as used in the context of the present invention relates primarily to antibodies, and fragments thereof, but can also refer to other non-antibody molecules that bind to α-synuclein including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin, immunoglobulin (Ig) superfamilies, and synthetic binding molecules. Thus, for the sake of clarity only and without restricting the scope of the present invention most of the following embodiments are discussed with respect to antibodies and antibody-like molecules which represent exemplary binding molecules for the development of therapeutic and diagnostic agents.

The terms "antibody" and "immunoglobulin" are used interchangeably herein. An antibody or immunoglobulin is an α-synuclein-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains. Any antibody or immunoglobulin fragment which contains sufficient structure to specifically bind to α-synuclein is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a f-sheet conformation and the CDRs form loops which connect, and in some cases form part of, the f-sheet structure. Thus, framework regions act to form a scaffold that provides for positioning the CDRs in correct orientation by interchain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In one embodiment, the antibody of the present invention is not a polyclonal antibody, i.e. it substantially consists of one particular antibody species rather than being a mixture obtained from a plasma immunoglobulin sample.

Antibody fragments, including single-chain antibodies, can comprise the variable region(s) alone or in combination with the entirety or a portion of the following: hinge region, CH1, CH2, and CH3 domains. Also included in the invention are α-synuclein-binding fragments also comprising any combination of variable region(s) with a hinge region, CH1, CH2, and CH3 domains. Antibodies or immunospecific fragments thereof of the present invention can be from any animal origin including birds and mammals. In certain embodiments, the antibodies are human, murine, donkey, rabbit, goat, guinea pig, camel, llama, horse, or chicken antibodies. In another embodiment, the variable region can be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (vbase.mrc-cpe.cam.ac.uk) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural α-synuclein in its relevant conformation in the human body, (ii) having protected the individual or is at least significant for the presence of α-synuclein, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote an α-synuclein binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, or about 95% or more identical. Hence, in some embodiments, a full length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer can comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. In one embodiment, the light chain portion comprises at least one of a VL or CL domain.

The minimum size of a peptide or polypeptide epitope for an antibody is thought to be about four to five amino acids. Peptide or polypeptide epitopes can contain, for example, at least seven, at least nine, or between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, at least 8, at least 9, at least 10, at least 15, at least 20, at least 25, or between about 15 to about 30 contiguous or non-contiguous amino acids of α-synuclein. As used herein, when an antibody is said to bind "within" a given range of amino acids, e.g., bind to an epitope "within amino acids 4 to 15 of α-synuclein," it is meant that the epitope encompasses the full range of stated amino acids or is smaller. In other words, for an epitope "within amino acids 4 to 15 of α-synuclein," the epitope can include the entire 12-amino acid peptide chain of 4 to 15, but can also be smaller, e.g., amino acids 4 to 12, amino acids 4 to 10 or amino acids 4 to 8. The person of ordinary skill in the art will also recognize that amino acids outside of the stated range may contribute to better binding affinity or increased recognition of a conformational epitope, but are not required for binding.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody can cross-react with the related epitope.

By way of non-limiting example, a binding molecule, e.g., an antibody binds a first epitope preferentially if it binds said first epitope with a dissociation constant ($K_D$) that is less than the antibody's $K_D$ for the second epitope. In another non-limiting example, an antibody binds a first antigen preferentially if it binds the first epitope with an affinity that is at least one order of magnitude less than the antibody's $K_D$ for the second epitope. In another non-limiting example, an antibody binds a first epitope preferentially if it binds the first epitope with an affinity that is at least two orders of magnitude less than the antibody's $K_D$ for the second epitope.

In another non-limiting example, a binding molecule, e.g., an antibody binds a first epitope preferentially if it binds the first epitope with an off rate (k(off)) that is less than the antibody's k(off) for the second epitope. In another non-limiting example, an antibody binds a first epitope preferentially if it binds the first epitope with an affinity that is at least one order of magnitude less than the antibody's k(off) for the second epitope. In another non-limiting example, an antibody binds a first epitope preferentially if it binds the first epitope with an affinity that is at least two orders of magnitude less than the antibody's k(off) for the second epitope.

In some embodiments binding molecule, e.g., an antibody or antigen-binding fragment, variant, or derivative disclosed herein can bind a α-synuclein or a fragment or variant thereof with an off rate (k(off)) of less than or equal to $5 \times 10^{-2}$ sec$^{-1}$, $10^{-2}$ sec$^{-1}$, $5 \times 10^{3}$ sec$^{-1}$ or $10^{3}$ sec$^{-1}$. In some embodiments, an antibody of the invention can bind α-synuclein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

In certain embodiments, a binding molecule, e.g., an antibody or antigen-binding fragment, variant, or derivative disclosed herein can bind α-synuclein or a fragment or variant thereof with an on rate (k(on)) of greater than or equal to $10^{3}$ M$^{-1}$ sec$^{-1}$, $5 \times 10^{3}$ M$^{-1}$ sec$^{-1}$, $10^{4}$ M$^{-1}$ sec$^{-1}$ or $5 \times 10^{4}$ M$^{-1}$ sec$^{-1}$. In some embodiments, an antibody of the invention can bind α-synuclein or a fragment or variant thereof with an on rate (k(on)) greater than or equal to $10^{5}$ M$^{-1}$ sec$^{-1}$, $5 \times 10^{5}$ M$^{-1}$ sec$^{-1}$, $10^{6}$ M$^{-1}$ sec$^{-1}$, or $5 \times 10^{6}$ M$^{-1}$ sec$^{-1}$ or $10^{7}$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. As an example, an antibody can competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N.Y. (1984), Kuby, Janis Immunology, W. H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, can be made with standardized solutions of antibody and antigen, and a standardized buffer.

Binding molecules, e.g., antibodies or antigen-binding fragments, variants or derivatives thereof of the invention can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. In some embodiments, an antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Binding molecules, e.g., antibodies or antigen-binding fragments, variants or derivatives thereof of the invention can also be described or specified in terms of their binding affinity to α-synuclein. Binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, cerebrospinal fluid ("CSF"), or urine. In other aspects, a sample can comprise whole blood, plasma, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 µl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

As used herein, the terms "treat" or "treatment" refer to both therapeutic treatment and prophylactic or preventative measures, wherein the object is to prevent or slow down (lessen) an undesired physiological change or disorder, such as the development of Parkinsonism. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

II. Antibodies

The present invention generally relates to human anti-α-synuclein antibodies and antigen-binding fragments thereof, which can demonstrate the immunological binding characteristics and/or biological properties as outlined for the antibodies illustrated in the Examples. In accordance with the present invention human monoclonal antibodies specific for α-synuclein were cloned from a pool of aged subjects.

In the course of the experiments performed in accordance with the present invention initial attempts failed to clone α-synuclein specific antibodies but almost always resulted in false-positive clones. Further investigation of these clones revealed that they produced antibodies recognizing proteins of *E. coli*. In order to circumvent this problem, antibodies in conditioned media of human memory B cell cultures were screened in parallel for binding to coated full-length alpha synuclein monomer and absence of binding to *E. coli*. proteins and bovine serum albumin (BSA). In particular, B cell conditioned medium was preabsorbed with *E. coli* proteins prior to subjecting the medium to an ELISA assay for screening of α-synuclein binding human antibodies.

Initial attempts at isolating specific antibodies were focused at pools of human subjects with high plasma binding activity to α-synuclein, suggestive of elevated levels of circulating α-synuclein antibodies plasma. These attempts failed to produce α-synuclein specific human memory B cells and the antibodies described in the current invention were isolated from pools of subjects with low plasma reactivity to α-synuclein.

Due to this measure, several antibodies were isolated. Selected antibodies were further analyzed for class and light chain subclass determination. Selected relevant antibody messages from memory B cell cultures are then transcribed by RT-PCR, cloned and combined into expression vectors for recombinant production; see PCT Publication No. WO 2010/069603 A1. Exemplary anti-human α-synuclein antibodies NI-202.12F4, NI-202.3G12, and NI-202.3D8 are disclosed in PCT Publication No. WO 2010/069603 A1

Disclosed herein is human monoclonal antibody NI-202.21D11. Recombinant expression of NI-202.21D11 in HEK293 or CHO cells and subsequent characterization of its binding specificity for human α-synuclein (FIG. 2A-B) was determined. Thus, one aspect of the present invention relates to the isolated human monoclonal anti-α-synuclein antibody NI-202. 21D11 and antigen-binding fragments, derivatives and variants thereof. The present invention is also drawn to a binding molecule such as an antibody, or antigen-binding fragment, variant or derivatives thereof, where the antibody comprises a VH with the amino acid sequence of SEQ ID NO:15 or SEQ ID NO:20, and a VL with the amino acid sequence of SEQ ID NO:22 or SEQ ID NO:26, or antigen-binding fragments, variants or derivatives thereof. In one embodiment, NI-202.21D11, as well as variants, fragments, or derivatives thereof are characterized as specifically binding human α-synuclein compared to human β-synuclein and human γ-synuclein, and to human α-synuclein as compared to murine α-synuclein. NI-202. 21D11 preferentially binds to α-synuclein in the oligomeric or aggregated form.

In one embodiment, the present invention is directed to an anti-α-synuclein antibody, or antigen-binding fragment, variant or derivatives thereof, where the antibody specifically binds to the same epitope of α-synuclein as the reference antibody NI-202.21D11. As illustrated in the Examples, antibody NI-202. 21D11 binds to α-synuclein truncations containing the C-terminal acidic region (amino acids 96-140) in a direct ELISA assay, e.g., within amino acids 113 to 123 of SEQ ID NO:1, and specifically binds to an epitope within the amino acids PVDPDNE (amino acids 117-123 of SEQ ID NO:1).

Antibody NI-202. 21D11 preferentially binds to α-synuclein aggregates or fibrils over the monomeric form of α-synuclein as shown in Example 2. Furthermore, antibody NI-202. 21D11 binds to pathological forms of α-synuclein in brain, e.g. pathological aggregates of α-synuclein as exemplified by immunohistochemical staining described in Example 3. Hence, the present invention provides a new human anti-α-synuclein antibody useful for diagnostic and therapeutic purposes.

In one embodiment, the present invention provides binding molecules, e.g., antibodies or antigen-binding fragments, variants, or derivatives thereof which exhibit the precise binding properties of the exemplary NI-202.12F4 antibody as described in PCT Publication No. WO 2010/069603 A1. The present invention provides binding molecules which bind to an epitope at the N-terminus of α-synuclein, e.g., binding molecules which bind within amino acids 4 to 15 of SEQ ID NO: 1. Certain embodiments provide binding molecules, e.g., antibodies or antigen-binding fragments, variants or derivatives thereof, which bind within amino acids 4 to 15 of SEQ ID NO:1, but excluding antibodies comprising a VH (SEQ ID NO:5 or SEQ ID NO:9), VL (SEQ ID NO:10 or SEQ ID NO:14), VHCDR1 (SEQ ID NO:6), VHCDR2 (SEQ ID NO:7), VHCDR3 (SEQ ID NO:8), VLCDR1 (SEQ ID NO: 11), VLCDR2 (SEQ ID NO: 12) and/or VLCDR3 (SEQ ID NO: 13) of NI-202.12F4, or fragments, variants, or derivatives thereof.

The present invention further provides binding molecules, e.g. antibodies and antigen-binding fragments, variants, or derivatives thereof, which comprises at least one, two, three, four, five, or six complementarity determining regions (CDRs) of a NI-202. 21D11 VH and/or VL variable region comprising any one of the amino acid sequences depicted in FIG. 1. The corresponding nucleotide sequences encoding the above-identified variable regions are set forth in the attached sequence listing. An exemplary set of CDRs of the above amino acid sequences of the VH and/or VL region as depicted in FIG. 1 is also indicated in the appended sequence listing. However, as discussed in the following the person skilled in the art is well aware of the fact that in addition or alternatively CDRs can be used, which differ in their amino acid sequence from those set forth in FIG. 1 by one, two, three, four, five, or more amino acids. The VH of NI-202. 21D11 is represented by amino acid sequence SEQ ID NO:15 and DNA sequence SEQ ID NO:19, and its GL-corrected form is represented as amino acid sequence SEQ ID NO:20 and DNA sequence SEQ ID NO:21. The VL of NI-202. 21D11 is represented by amino acid sequence SEQ ID NO:22 and DNA sequence SEQ ID NO:28, and its GL-corrected form is represented as amino acid sequence SEQ ID NO:26 and DNA sequence SEQ ID NO:27. The heavy chain CDR amino acid sequences of VH-CDR1, VH-CDR2 and VH-CDR3 are represented by SEQ ID NO:16, SEQ ID NO:17, and SEQ ID NO:18, respectively. The light chain CDR amino acid sequences of VL-CDR1, VL-CDR2 and VL-CDR3 are represented by SEQ ID NO:23, SEQ ID NO:24, and SEQ ID NO:25, respectively.

In one embodiment, a binding molecule, e.g., an antibody or antigen binding fragment, variant, or derivative thereof of the present invention is any one of the antibodies comprising an amino acid sequence of the VH and/or VL region as depicted in FIG. 1. Alternatively, the antibody of the present invention is a binding molecule, e.g., an antibody or antigen binding fragment, variant, or derivative thereof which competes for binding to α-synuclein with an antibody having a VH and/or VL region as depicted in FIG. 1. Those antibodies can be human as well, in particular for therapeutic applications. Alternatively, the antibody is a murine, murinized and chimeric murine-human antibody, which are particularly useful for diagnostic methods and studies in animals.

As mentioned above, due to its generation upon a human immune response the human monoclonal antibody of the present invention will recognize epitopes which are of particular physiological relevance and which might not be accessible or less immunogenic in case of immunization processes for the generation of for example mouse monoclonal antibodies and in in vitro screening of phage display libraries, respectively. Accordingly, an epitope of a human anti-α-synuclein antibody of the present invention can be unique. Therefore, the present invention also extends generally to anti-α-synuclein antibodies and α-synuclein binding molecules which compete with the human monoclonal antibody of the present invention for specific binding to α-synuclein. The present invention is more specifically directed to a binding molecule, e.g., an antibody, or antigen-binding fragment, variant or derivatives thereof, where the antibody specifically binds to the same epitope of α-synuclein as the reference antibody NI-202.21D11.

Competition between antibodies can be determined, for example, by an assay in which the immunoglobulin under test inhibits specific binding of a reference antibody to a common antigen, such as α-synuclein. Numerous types of competitive binding assays are known, for example: solid phase direct or indirect radioimmunoassay (MA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label MA using $I^{125}$ label; see Morel et al, Molec. Immunol. 25 (1988), 7-15 and Moldenhauer et al., Scand. J. Immunol. 32 (1990), 77-82. Typically, such an assay involves the use of purified α-synuclein or aggregates thereof bound to a solid surface or cells bearing either of these, an unlabelled test immunoglobulin and a labeled reference immunoglobulin, i.e. a human monoclonal antibody of the present invention. Competitive inhibition is measured by determining the amount of label bound to the solid surface or cells in the presence of the test immunoglobulin. Usually the test immunoglobulin is present in excess. A competitive binding assay can be performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to a binding molecule, e.g., an antibody, or antigen-binding fragment, variant or derivatives thereof, where the antibody competitively inhibits the reference antibody NI-202. 21D11 from binding to α-synuclein.

Also disclosed is an isolated binding molecule, e.g., an antibody or antigen-binding fragment thereof which specifically binds to human α-synuclein, comprising an immunoglobulin heavy chain variable region (VH) amino acid sequence at least 80%, 85%, 90% 95% or 100% identical to SEQ ID NO:15 or SEQ ID NO:20.

Further disclosed is an isolated binding molecule, e.g., an antibody or antigen-binding fragment thereof which specifically binds to human α-synuclein, comprising a VH amino acid sequence identical to, or identical except for one, two, three, four, five, or more amino acid substitutions to SEQ ID NO:15 or SEQ ID NO:20.

Also disclosed is an isolated binding molecule, e.g., an antibody or antigen-binding fragment thereof which specifically binds to human α-synuclein, comprising an immunoglobulin light chain variable region (VL) amino acid sequence at least 80%, 85%, 90% 95% or 100% identical to SEQ ID NO:22 or SEQ ID NO:26.

Some embodiments disclose an isolated binding molecule, e.g., an antibody or antigen-binding fragment thereof which specifically binds to human α-synuclein, comprising a VL amino acid sequence identical to, or identical except for one, two, three, four, five, or more amino acid substitutions, to SEQ ID NO:22 or SEQ ID NO:26.

In other embodiments, an isolated antibody or antigen-binding fragment thereof which specifically binds to human α-synuclein comprises, consists essentially of, or consists of VH and VL amino acid sequences at least 80%, 85%, 90% 95% or 100% identical to: (a) SEQ ID NO:15 and SEQ ID NO:22, respectively, (b) SEQ ID NO:15 and SEQ ID NO:26, respectively, (c) SEQ ID NO:20 and SEQ ID NO:22, respectively, (d) SEQ ID NO:20 and SEQ ID NO:26, respectively.

Also disclosed is an isolated binding molecule, e.g., an antibody or antigen-binding fragment thereof which specifically binds to human α-synuclein, comprising, consisting essentially of, or consisting of an immunoglobulin heavy chain variable region (VH), where at least one, two or all three VH-CDRs of the heavy chain variable region are at least 80%, 85%, 90% or 95% identical to reference heavy chain VH-CDR1, VH-CDR2 or VH-CDR3 amino acid sequences in FIG. 1, and represented by SEQ ID NO:16, SEQ ID NO:17, and SEQ ID NO:18, respectively. Thus, according to this embodiment a heavy chain variable region of the invention has VH-CDR1, VH-CDR2 and VH-CDR3 polypeptide sequences related to the VH-CDR1, VH-CDR2 and VH-CDR3 amino acid sequences represented by SEQ ID NO:16, SEQ ID NO:17, and SEQ ID NO:18, respectively. While FIG. 1 shows VH-CDRs defined by the Kabat system, other CDR definitions, e.g., VH-CDRs defined by the Chothia system, are also included in the present invention, and can be easily identified by a person of ordinary skill in the art using the sequence data presented.

Also disclosed is an isolated binding molecule, e.g., an antibody or antigen-binding fragment thereof which specifically binds to human α-synuclein, comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 amino acid sequences represented by SEQ ID NO:16, SEQ ID NO:17, and SEQ ID NO:18, respectively.

Also disclosed is an isolated binding molecule, e.g., an antibody or antigen-binding fragment thereof which specifically binds to human α-synuclein, comprising, consisting essentially of, or consisting of an immunoglobulin heavy chain variable region (VH) in which the VH-CDR1, VH-CDR2 and VH-CDR3 regions have polypeptide sequences which are identical to, or identical except for one, two, three, four, five, or six amino acid substitutions in any one VH-CDR, to the VH-CDR1, VH-CDR2 or VH-CDR3 amino acid sequences represented by SEQ ID NO:16, SEQ ID NO:17, and SEQ ID NO: 18, respectively. Also provided is an immunoglobulin heavy chain variable region (VH) in which the VH-CDR1, VH-CDR2 and VH-CDR3 regions have polypeptide sequences which are identical to, or identical except for five, six, seven, eight, nine, ten, eleven, twelve, thirteen, fourteen, fifteen, or twenty total CDR substitutions to amino acid sequences represented by SEQ ID NO:16, SEQ ID NO:17, and SEQ ID NO:18, respectively. In certain embodiments the amino acid substitutions are conservative.

Also disclosed is an isolated binding molecule, e.g., an antibody or antigen-binding fragment thereof which specifically binds to human α-synuclein, comprising, consisting essentially of, or consisting of an immunoglobulin light chain variable region (VL), where at least one, two, or all three of the VL-CDRs of the light chain variable region are at least 80%, 85%, 90% or 95% identical to reference light chain VL-CDR1, VL-CDR2 or VL-CDR3 amino acid sequences represented by SEQ ID NO:23, SEQ ID NO:24, and SEQ ID NO:25, respectively. Thus, according to this embodiment a light chain variable region of the invention has VL-CDR1, VL-CDR2 and VL-CDR3 polypeptide sequences related to the polypeptides shown in FIG. 1 and represented by SEQ ID NO:23, SEQ ID NO:24, and SEQ ID NO:25, respectively. While FIG. 1 shows VL-CDRs defined by the Kabat system, other CDR definitions, e.g., VL-CDRs defined by the Chothia system, are also included in the present invention.

Also disclosed is an isolated binding molecule, e.g., an antibody or antigen-binding fragment thereof which specifically binds to human α-synuclein, comprising, consisting essentially of, or consisting of an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in FIG. 1 and represented by SEQ ID NO:23, SEQ ID NO:24, and SEQ ID NO:25, respectively.

Also disclosed is an isolated binding molecule, e.g., an antibody or antigen-binding fragment thereof which specifically binds to human α-synuclein, comprising, consisting essentially of, or consisting of an immunoglobulin light chain variable region (VL) in which the VL-CDR1, VL-CDR2 and VL-CDR3 regions have polypeptide sequences which are identical to, or identical except for one, two, three, four, five, or six amino acid substitutions in any one VL-CDR, to the VL-CDR1, VL-CDR2 or VL-CDR3 amino acid sequences represented by SEQ ID NO:23, SEQ ID NO:24, and SEQ ID NO:25, respectively. Also provided is an immunoglobulin light chain variable region (VL) in which the VL-CDR1, VL-CDR2 and VL-CDR3 regions have polypeptide sequences which are identical to, or identical except for five, six, seven, eight, nine, ten, eleven, twelve, thirteen, fourteen or fifteen total CDR substitutions to amino acid sequences represented by SEQ ID NO:23, SEQ ID NO:24, and SEQ ID NO:25, respectively. In certain embodiments the amino acid substitutions are conservative.

An immunoglobulin or its encoding cDNA can be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, an antibody of the invention can exist in a variety of forms besides complete antibodies; including, for example, Fv, Fab and F(ab)2, as well as in single chains, such as scFvs; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides can easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the human anti-α-synuclein antibodies of the present invention and display the mentioned properties, i.e. which specifically recognize α-synuclein. Such antibodies and binding molecules can be tested for their binding specificity and affinity by ELISA and Western Blot and immunohistochemistry as described herein, see, e.g., the Examples. Furthermore, preliminary results of subsequent experiments performed in accordance with the present invention revealed that the human anti-α-synuclein antibody of the present invention, in particular antibody NI-202. 21D11 recognizes α-synuclein inclusion bodies present on human brain sections of patients who suffered from dementia with Lewy bodies (DLB) or Parkinson's disease (PD). Thus, in one embodiment of the present invention, the human antibody or binding fragment, derivative or variant thereof recognizes α-synuclein on human DLB or PD brain sections (see, e.g., FIG. 4c).

Immortalized B cells or B memory cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. Nucleotide sequences can be engineered to remove undesired motifs (such as splice sites or restriction sties), and the codon usage can be optimized for the cell in which the antibody or fragment thereof is to be expressed. In addition, one or more mutations which alter amino acids in the variable regions can be made, e.g., to increase affinity or improve stability. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells can be used; for efficient processing. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. Expression systems can be designed to include signal peptides so that the resulting antibodies are secreted into the medium; however, intracellular production is also possible.

In accordance with the above, the present invention also relates to a polynucleotide encoding the antibody or equivalent binding molecule of the present invention, one or more CDRs, one or more of a heavy chain or light chain variable regions or variants thereof, of an immunoglobulin chain of the anti-α-synuclein antibodies described above.

The person skilled in the art will readily appreciate that the variable domain of an antibody, or any portion thereof can be used for the construction of other polypeptides or antibodies of desired specificity and biological function. Thus, the present invention also provides polypeptides and antibodies comprising at least one heavy chain or light chain CDR, or such CDR with 1, 2, 3, 4, or more amino acid substitutions, of antibody NI-202. 21D11, which can have substantially the same or similar binding properties as NI-202.21D11, described in the appended examples. The person skilled in the art knows that binding affinity can be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more amino acid substitutions. In certain embodiments, an antibody of the invention comprises in one or both of its immunoglobulin chains two or all three CDRs of the variable regions (original or corrected) as set forth in FIG. 1.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region can activate the complement system. Activation of complement is important in the opsonization and lysis of cell pathogens. The activation of complement also stimulates the inflammatory response and can also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of α-synuclein aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies can be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion can be mutated to decrease effector function using techniques known in the art. For example, the deletion or inactivation (through point mutations or other means) of a constant region domain can reduce Fc receptor binding of the circulating modified antibody thereby increasing α-synuclein localization. In other cases, constant region modifications consistent with the instant invention moderate complement binding and thus reduce the serum half life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as α-synuclein localization, biodistribution and serum half-life, can easily be measured and quantified using well know immunological techniques without undue experimentation.

In certain antibodies, or antigen-binding fragments, variants, or derivatives thereof described herein, the Fc portion can be mutated or exchanged for alternative protein sequences to increase the cellular uptake of antibodies by way of example by enhancing receptor-mediated endocytosis of antibodies via Fcγ receptors, LRP, or Thy 1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences biding to α-synuclein as well as a cell surface receptor can be engineered using techniques known in the art.

In certain antibodies, or antigen-binding fragments, variants, or derivatives thereof described herein, the Fc portion can be mutated or exchanged for alternative protein sequences or the antibody can be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids.

In certain embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, VH and VL sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., α-synuclein-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: *Monoclonal Antibodies and T-Cell Hybridomas* Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that can contain one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones can be subcloned by limiting dilution procedures and grown by standard methods; see, e.g., Goding, *Monoclonal Antibodies: Principles and Practice*, Academic Press, pp 59-103 (1986). It will further be appreciated that the monoclonal antibodies secreted by the subclones can be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines can be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibody fragments that recognize specific epitopes can be generated by known techniques. For example, Fab and F(ab')$_2$ fragments can be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Completely human antibodies, such as described herein, are particularly desirable for therapeutic treatment of human patients. Human antibodies of the present invention are isolated, e.g., from elderly subjects who because of their age may be suspected to be at risk of developing a disorder, e.g., Parkinson's disease, or a patient with the disorder but with an unusually stable disease course. However, though it is prudent to expect that elderly healthy and symptom-free subjects, respectively, more regularly will have developed protective anti-α-synuclein antibodies than younger subjects, the latter can be used as well as source for obtaining a human antibody of the present invention. This is particularly true for younger patients who are predisposed to develop a familial form of a synucleinopathic disease but remain symptom-free since their immune system and response functions more efficiently than that in older adults.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide can be substituted for the deleted domain to provide flexibility and freedom of movement for the variable region. Domain deleted constructs can be derived using a vector encoding an IgG$_1$ human constant domain, see, e.g., international applications WO02/060955 and WO02/096948A2. This vector is engineered to delete the CH2 domain and provide a synthetic vector expressing a domain deleted IgG$_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain can be enough to substantially reduce Fc binding and thereby increase α-synuclein localization. Similarly, one or more constant region domains that control the effector function (e.g. complement binding) can be deleted. Such partial deletions of the constant regions can improve selected characteristics of the antibody (serum half-life) while leaving other desirable functions associated with the subject constant region domain intact. Moreover, as alluded to above, the constant regions of the disclosed antibodies can be synthetic through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention also provides antibodies that comprise, consist essentially of, or consist of, variants (including derivatives) of antibody molecules (e.g., the VH regions and/or VL regions) described herein, which antibodies or fragments thereof immunospecifically bind to α-synuclein. Standard techniques known to those of skill in the art can be used to introduce mutations in the nucleotide sequence encoding an antibody, including, but not limited to, site-directed mutagenesis and PCR-mediated mutagenesis which result in amino acid substitutions. Variants (including derivatives) can encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VH-CDR1, VH-CDR2, VH-CDR3, VL region, VL-CDR1, VL-CDR2, or VL-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind α-synuclein).

For example, it is possible to introduce mutations only in framework regions or only in CDR regions of an antibody molecule. Introduced mutations can be silent or neutral missense mutations, e.g., have no, or little, effect on an antibody's ability to bind antigen, indeed some such mutations do not alter the amino acid sequence whatsoever. These types of mutations can be useful to optimize codon usage, or improve a hybridoma's antibody production. Codon-optimized coding regions encoding antibodies of the present invention are disclosed elsewhere herein. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein can routinely be expressed and the functional and/or biological activity of the encoded protein, (e.g., ability to immunospecifically bind at least one epitope of α-synuclein) can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxribonucleotide, which can be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions can be made at one or more non-essential amino acid residues.

As is well known, RNA can be isolated from the original B cells, hybridoma cells or from other transformed cells by standard techniques, such as guanidinium isothiocyanate extraction and precipitation followed by centrifugation or chromatography. Where desirable, mRNA can be isolated from total RNA by standard techniques such as chromatography on oligo dT cellulose. Suitable techniques are familiar in the art. In one embodiment, cDNAs that encode the light and the heavy chains of the antibody can be made, either simultaneously or separately, using reverse transcriptase and DNA polymerase in accordance with well known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as human constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic according to the present invention at any point during the isolation process or subsequent analysis.

One embodiment provides an isolated polynucleotide comprising, consisting essentially of, or consisting of a nucleic acid encoding an immunoglobulin heavy chain variable region (VH) amino acid sequence at least 80%, 85%, 90% 95% or 100% identical to SEQ ID NO: 15 or SEQ ID NO:20.

Another embodiment provides an isolated polynucleotide comprising, consisting essentially of, or consisting of a nucleic acid encoding a VH amino acid sequence identical to, or identical except for one, two, three, four, five, or more amino acid substitutions to SEQ ID NO:15 or SEQ ID NO:20.

Another embodiment provides an isolated polynucleotide comprising, consisting essentially of, or consisting of a nucleic acid encoding an immunoglobulin heavy chain variable region (VH), where at least one, two or all three of the CDRs of the heavy chain variable region are at least 80%, 85%, 90% or 95% identical to reference heavy chain VH-CDR1, VH-CDR2 or VH-CDR3 amino acid sequences represented by SEQ ID NO:16, SEQ ID NO:17, and SEQ ID NO:18, respectively. Thus, this embodiment provides an isolated polynucleotide encoding a heavy chain variable region of the invention which has VH-CDR1, VH-CDR2 and VH-CDR3 amino acid sequences related to those represented by SEQ ID NO:16, SEQ ID NO:17, and SEQ ID NO:18, respectively, as shown in FIG. 1.

In another embodiment, the present invention provides an isolated polynucleotide comprising, consisting essentially of, or consisting of a nucleic acid encoding an immunoglobulin heavy chain variable region (VH) in which the VH-CDR1, VH-CDR2, and VH-CDR3 regions have polypeptide sequences which are identical to the VH-CDR1, VH-CDR2, and VH-CDR3 groups represented by SEQ ID NO:16, SEQ ID NO:17, and SEQ ID NO:18, respectively, as shown in FIG. 1.

A further embodiment provides an isolated binding molecule e.g., an antibody or antigen-binding fragment comprising the VH encoded by the polynucleotide which specifically or preferentially binds to human α-synuclein.

Another embodiment provides an isolated polynucleotide comprising, consisting essentially of, or consisting of a nucleic acid encoding an immunoglobulin light chain variable region (VL) amino acid sequence at least 80%, 85%, 90% 95% or 100% identical to SEQ ID NO:22 or SEQ ID NO:26.

A further embodiment provides an isolated polynucleotide comprising, consisting essentially of, or consisting of a nucleic acid encoding a VL amino acid sequence identical to, or identical except for one, two, three, four, five, or more amino acid substitutions to SEQ ID NO:22 or SEQ ID NO:26.

Another embodiment provides an isolated polynucleotide comprising, consisting essentially of, or consisting of a nucleic acid encoding an immunoglobulin light chain variable region (VL), where at least one, two, or all three of the VL-CDRs of the light chain variable region are at least 80%, 85%, 90% or 95% identical to reference light chain VL-CDR1, VL-CDR2 or VL-CDR3 amino acid sequences represented by SEQ ID NO:23, SEQ ID NO:24, and SEQ ID NO:25, respectively. Thus, this embodiment provides an isolated polynucleotide encoding a light chain variable region of the invention which has VL-CDR1, VL-CDR2 and VL-CDR3 amino acid sequences related to those represented by SEQ ID NO:23, SEQ ID NO:24, and SEQ ID NO:25, respectively, as shown in FIG. 1.

In another embodiment, the present invention provides an isolated polynucleotide comprising, consisting essentially of, or consisting of a nucleic acid encoding an immunoglobulin light chain variable region (VL) in which the VL-CDR1, VL-CDR2, and VL-CDR3 regions have polypeptide sequences which are identical to the VH-CDR1, VH-CDR2, and VH-CDR3 groups represented by SEQ ID NO:16, SEQ ID NO:17, and SEQ ID NO:18, respectively, as shown in FIG. 1.

A further embodiment provides an isolated binding molecule e.g., an antibody or antigen-binding fragment comprising the VL encoded by the polynucleotide which specifically or preferentially binds to human α-synuclein.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In one embodiment of the present invention, the polynucleotide comprises, consists essentially of, or consists of a nucleic acid having a polynucleotide sequence of the VH set forth in SEQ ID NO:19 or SEQ ID NO:21, or the VL set forth in SEQ ID NO:27 or SEQ ID NO:28. In this respect, the person skilled in the art will readily appreciate that the polynucleotides encoding at least the variable domain of the light and/or heavy chain can encode the variable domain of both immunoglobulin chains or only one.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides can be produced or manufactured by any method known in the art. For example, if the nucleotide sequence of the antibody is known, a polynucleotide encoding the antibody can be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, such as polyA+ RNA, isolated from, any tissue or cells expressing the α-synuclein-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

Once the nucleotide sequence and corresponding amino acid sequence of the antibody, or antigen-binding fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that can be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (e.g., containing the heavy or light chain variable domain), of the invention has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors can include the nucleotide sequence encoding the constant region of the antibody molecule (see, e.g., international applications WO 86/05807 and WO 89/01036; and U.S. Pat. No. 5,122,464) and the variable domain of the antibody can be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems can be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements can also be added for optimal synthesis of mRNA. These elements can include signal sequences, splice signals, as well as transcriptional promoters, enhancers, and termination signals.

In certain embodiments the cloned variable region genes are inserted into an expression vector along with the heavy and light chain constant region genes (e.g., human) as discussed above. In one embodiment, this is effected using a proprietary expression vector of Biogen IDEC, Inc., referred to as NEOSPLA, disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells can be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the antibodies, or antigen-binding fragments, variants, or derivatives thereof of the invention can be expressed using polycistronic constructs such as those disclosed in US patent application publication no.

2003-0157641 A1 and incorporated herein in its entirety. In these expression systems, multiple gene products of interest such as heavy and light chains of antibodies can be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems can be used to effectively produce the full range of antibodies disclosed in the instant application.

More generally, once the vector or DNA sequence encoding a monomeric subunit of the antibody has been prepared, the expression vector can be introduced into an appropriate host cell. Introduction of the plasmid into the host cell can be accomplished by various techniques well known to those of skill in the art. These include, but are not limited to, transfection including lipotransfection using, e.g., Fugene or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. For the expression of double-chained antibodies, vectors encoding both the heavy and light chains can be inserted into a host cell for expression of the entire immunoglobulin molecule, as detailed below.

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains can comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibody molecules for use in the methods described herein. Such host-expression systems represent vehicles by which the coding sequences of interest can be produced and subsequently purified, but also represent cells which can, when transformed or transfected with the appropriate nucleotide coding sequences, express an antibody molecule of the invention in situ. These include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, W138, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1clBPT (bovine endothelial cells), RAJI (human lymphocyte) and 293 (human kidney). Host cell lines are typically available from commercial services, the American Tissue Culture Collection or from published literature.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is used. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells are allowed to grow for, e.g., 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

A number of selection systems can be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, *The use of vectors based on gene amplification for the expression of cloned genes in mammalian cells in DNA cloning*, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or immuno-affinity chromatography, e.g., after preferential biosynthesis of a synthetic hinge region polypeptide or prior to or subsequent to the HIC chromatography step described herein.

Genes encoding antibodies, or antigen-binding fragments, variants, or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be used. Such vectors include, but are not limited, to the *E. coli* expression vector pUR278 (Ruther et al., EMBO J. 2 (1983), 1791), in which the antibody coding sequence can be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, a method for increasing the affinity of antibodies of the invention is disclosed in US patent publication 2002-0123057 A1.

V. Fusion Proteins and Conjugates

In certain embodiments, the antibody polypeptide comprises an amino acid sequence or one or more moieties not normally associated with an antibody. Exemplary modifications are described in more detail below. For example, in some embodiments a single-chain fv antibody fragment of the invention can comprise a flexible linker sequence, or can be modified to add a functional moiety (e.g., PEG, a drug, a toxin, or a label such as a fluorescent, radioactive, enzyme, nuclear magnetic, heavy metal and the like)

In certain embodiments, an antibody polypeptide of the invention comprises, consists essentially of, or consists of a fusion protein. Fusion proteins are chimeric molecules which comprise, for example, an immunoglobulin α-synuclein-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention can further be recombinantly fused to a heterologous polypeptide at the N- or C-terminus or chemically conjugated (including covalent and non-covalent conjugations) to polypeptides or other compositions. For example, antibodies can be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and can contain amino acids other than the 20 gene-encoded amino acids. Antibodies can be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification can be present in the same or varying degrees at several sites in a given antibody. Also, a given antibody can contain many types of modifications. Antibodies can be branched, for example, as a result of ubiquitination, and they can be cyclic, with or without branching. Cyclic, branched, and branched cyclic antibodies can result from posttranslation natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the VH regions of an antibody of the invention or the amino acid sequence of any one or more of the VL regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the VH-CDRs of an antibody, or fragments, variants, or derivatives thereof, or the amino acid sequence of any one, two, three of the VL-CDRs of an antibody, or fragments, variants, or derivatives thereof, and a heterologous polypeptide sequence. In one embodiment, the fusion protein comprises a polypeptide having the amino acid sequence of a VH-CDR3 of an antibody of the present invention, or fragment, derivative, or variant thereof, and a heterologous polypeptide sequence, which fusion protein specifically binds to α-synuclein. In another embodiment, a fusion protein comprises a polypeptide having the amino acid sequence of at least one VH region of an antibody of the invention and the amino acid sequence of at least one VL region of an antibody of the invention or fragments, derivatives or variants thereof, and a heterologous polypeptide sequence. In some embodiments, the VH and VL regions of the fusion protein correspond to a single source antibody (or scFv or Fab fragment) which specifically binds α-synuclein. In yet another embodiment, a fusion protein for use in the diagnostic and treatment methods disclosed herein comprises a polypeptide having the amino acid sequence of any one, two, three or more of the VH CDRs of an antibody and the amino acid sequence of any one, two, three or more of the VL CDRs of an antibody, or fragments or variants thereof, and a heterologous polypeptide sequence. In certain embodiments, two, three, four, five, six, or more of the VH-CDR(s) or VL-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention can be fused to heterologous polypeptides to increase the in vivo half life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In certain embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made can be selected empirically to optimize the secretion or binding characteristics of the fusion protein. DNA encoding the fusion protein is then transfected into a host cell for expression.

Antibodies of the present invention can be used in non-conjugated form or can be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention can be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins can be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates can also be assembled using a variety of techniques depending on the selected agent to be conjugated. For example, conjugates with biotin are prepared e.g. by reacting an α-synuclein binding polypeptide with an activated ester of biotin such as the biotin N-hydroxysuccinimide ester. Similarly, conjugates with a fluorescent marker can be prepared in the presence of a coupling agent, e.g. those listed herein, or by reaction with an isothiocyanate, such as fluorescein-isothiocyanate. Conjugates of the antibodies, or antigen-binding fragments, variants, or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a neurological disease, to indicate the risk of getting a neurological disease, to monitor the development or progression of a neurological disease, i.e. synucleinopathic disease as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody will react with an appropriate substrate, such as a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnoni et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned α-synuclein binding molecule, e.g., antibody or antigen-binding fragment thereof of the present invention or derivative or variant thereof, or the polynucleotide, vector or cell of the invention. The composition of the present invention can further comprise a pharmaceutically acceptable carrier. Furthermore, the pharmaceutical composition of the present invention can comprise further agents such as interleukins or interferons depending on the intended use of the pharmaceutical composition. For example, for use in the treatment of Parkinson's disease the additional agent can be selected from the group consisting of small organic molecules, anti-α-synuclein antibodies, and combinations thereof. Hence, in one embodiment the present invention relates to the use of the α-synuclein binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a synucleinopathic disease, monitoring the progression of a synucleinopathic disease or a response to a synucleinopathic disease treatment in a subject or for determining a subject's risk for developing a synucleinopathic disease.

Hence, in one embodiment the present invention relates to a method of treating a neurological disorder characterized by abnormal accumulation and/or deposition of α-synuclein in the brain and the central nervous system, respectively, which method comprises administering to a subject in need thereof a therapeutically effective amount of an anti-α-synuclein binding molecule, antibody, polynucleotide, vector or cell of the instant invention. In certain embodiments NI-202. 21D11 or a fragment, variant or derivative thereof is delivered. The term "neurological disorder" includes but is not limited to synucleinopathic diseases such as Parkinson's disease (PD), dementia with Lewy bodies (DLB), and multiple systems atrophy (MSA). Unless stated otherwise, the terms neurodegenerative, neurological or neuropsychiatric are used interchangeably herein.

A particular advantage of the therapeutic approach of the present invention lies in the fact that the antibodies of the present invention are derived from B cells or B memory cells from elderly subjects with no signs of Parkinsonism and thus are, with a certain probability, capable of preventing a clinically manifest synucleinopathic disease, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target α-synuclein molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-α-synuclein antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-α-synuclein antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of α-synuclein, and in particular applicable for the treatment of Parkinson's disease (PD), dementia with Lewy bodies (DLB), and multiple systems atrophy (MSA).

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions can be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations can be adjusted to a pH and isotonic state compatible with the nasal mucous membranes. Formulations for rectal or vaginal administration can be presented as a suppository with a suitable carrier.

Furthermore, whereas the present invention includes the now standard (though fortunately infrequent) procedure of drilling a small hole in the skull to administer a drug of the present invention, in a one aspect, the binding molecule, especially antibody or antibody based drug of the present invention can cross the blood-brain barrier, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Furthermore, the pharmaceutical composition of the invention can comprise further agents such as dopamine or psychopharmacologic drugs, depending on the intended use of the pharmaceutical composition.

Furthermore, a pharmaceutical composition can be formulated as a vaccine, for example, if the pharmaceutical composition of the invention comprises an anti-α-synuclein antibody or binding fragment, derivative or variant thereof for passive immunization. As mentioned in the background section, oligomeric species of α-synuclein have been reported extracellularly in plasma and CSF (El-Agnaf et al., FASEB J. 20 (2006), 419-425) and passive immunization studies in mouse models of Parkinson's disease show that extracellular mouse monoclonal antibodies against α-synuclein can reduce accumulation of intracellular α-synuclein aggregates (Masliah et al., Neuron, 46 (2005), 857-868). Accordingly it is prudent to expect that the human anti-α-synuclein antibodies and equivalent α-synuclein binding molecules of the present invention are particularly useful as a vaccine for the prevention or amelioration of synucleinopathic diseases such as PD, DLB and MSA.

In one embodiment, it is beneficial to use recombinant Fab (rFab) and single chain fragments (scFvs) of the antibody of the present invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (scFvs) of monoclonal antibody WO-2 which recognizes an epitope in the N-terminal region of Aβ. The engineered fragments were able to (i) prevent amyloid fibrillization, (ii) disaggregate preformed Aβ1-42 fibrils and (iii) inhibit Aβ1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

A further embodiment includes co-administration or sequential administration of other neuroprotective agents useful for treating a synucleinopathic disease. In one embodiment, the additional agent is comprised in the pharmaceutical composition of the present invention. Examples of neuroprotective agents which can be used to treat a subject include, but are not limited to, an acetylcholinesterase inhibitor, a glutamatergic receptor antagonist, kinase inhibitors, HDAC inhibitors, anti-inflammatory agents, divalproex sodium, or any combination thereof. Examples of other neuroprotective agents that can be used concomitant with pharmaceutical composition of the present invention are described in the art; see, e.g. international application WO2007/011907. In one embodiment, the additional agent is dopamine or a dopamine receptor agonist.

In a further embodiment of the present invention the α-synuclein binding molecules, in particular antibodies of the present invention can also be co-administered or administered before or after transplantation therapy with neural transplants or stem cell therapy useful for treating a synucleinopathic disease. Such approaches with transplants of embryonic mesencephalic neurons have been performed in patients with Parkinson's disease with the aim of replacing the neurons that are lost in the disease and reinstating dopaminergic neurotransmission in the striatum. After 11-16 years post transplantation, the grafted neurons were found to contain Lewy bodies and Lewy neurites. This spread of α-synuclein pathology from the host to the grated tissues can be prevented by co-administration of α-synuclein binding molecules, in particular antibodies of the present invention.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In certain embodiments, the therapeutic agent in the composition is present in an amount sufficient to restore or preserve normal behavior and/or cognitive properties in case of PD, DLB or other synucleinopathic diseases.

From the foregoing, it is evident that the present invention encompasses any use of an α-synuclein binding molecule comprising at least one CDR of NI-202. 21D11 or fragments, variants, or derivatives thereof, in particular for diagnosing and/or treatment of a synucleinopathic disease as mentioned above. The binding molecule can be an antibody of the present invention or an immunoglobulin chain thereof. In addition, the present invention relates to anti-idiotypic antibodies of any one of the mentioned antibodies described herein. These are antibodies or other binding molecules which bind to the unique antigenic peptide sequence located on an antibody's variable region near the antigen-binding site and are useful, e.g., for the detection of anti-α-synuclein antibodies in sample of a subject.

In another embodiment the present invention relates to a diagnostic composition comprising any one of the above described α-synuclein binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the α-synuclein binding molecules, in particular antibodies of the present invention are used in a method for the diagnosis of a disorder in an individual by obtaining a body fluid sample from the tested individual which can be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention can also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array can be used, which is for example loaded with antibodies or equivalent antigen-binding molecules of the present invention which specifically recognize α-synuclein. Design of microarray immunoassays is summarized in Kusnezow et al., Mol. Cell Proteomics 5 (2006), 1681-1696. Accordingly, the present invention also relates to microarrays loaded with α-synuclein binding molecules identified in accordance with the present invention.

In one embodiment, the present invention relates to a method of diagnosing a synucleinopathic disease in a subject, the method comprising:

(a) assessing the level, localization, conformation or a combination thereof of α-synuclein in a subject to be diagnosed with the antibody or fragment thereof of any one of the invention and (b) comparing the level, localization, conformation or combination thereof of α-synuclein in the subject to one or more reference standards derived from one or more control samples, wherein a difference or similarity between the level, localization, conformation or combination thereof of α-synuclein in the subject and the reference standard indicates whether the subject has a synucleinopathic disease.

The subject to be diagnosed can be asymptomatic or preclinical for the disease. The reference standard can be from a patient with a synucleinopathic disease, for example PD, DLB or MSA, where a similarity between the level, localization, conformation or combination thereof of α-synuclein in the subject to be diagnosed and the reference standard indicates that the subject to be diagnosed has a synucleinopathic disease. Alternatively, or in addition a reference standard is derived from a subject does not have a synucleinopathic disease. In certain embodiments, the subject to be diagnosed and the reference standard(s) are age-matched. The analysis can be done in vivo, or via a sample isolated from the subject to be diagnosed, e.g., any body fluid suspected to contain α-synuclein, for example a blood, CSF, or urine sample The level, localization, and/or conformation of α-synuclein can be assessed by any suitable method known in the art comprising, e.g., analyzing α-synuclein by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. In vivo imaging of α-synuclein can comprises positron emission tomography (PET), single photon emission tomography (SPECT), near infrared (NIR) optical imaging or magnetic resonance imaging (MRI).

Methods of diagnosing a synucleinopathic disease such as PD, DLB, or MSA, monitoring a synucleinopathic disease progression, and monitoring a synucleinopathic disease treatment using antibodies and related means which can be adapted in accordance with the present invention are also described in international application WO2007/011907. Similarly, antibody based detection methods for α-synuclein are described in international applications WO99/50300, WO2005/047860, WO2007/021255 and WO2008/103472, the disclosure content of all being incorporated herein by reference. Those methods can be applied as described but with an α-synuclein specific antibody, binding fragment, derivative or variant of the present invention.

These and other embodiments are disclosed and encompassed by the description and examples of the present invention. Further literature concerning any one of the materials, methods, uses and compounds to be employed in accordance with the present invention can be retrieved from public libraries and databases, using for example electronic devices. For example the public database "Medline" can be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. The following experiments in Examples 1 and 2 are illustrated and described with respect to antibody NI-202.3G12, NI-202.12F4, and NI-202.3D8 as cloned, i.e. containing primer induced mutations at the very N-termini of the framework 1 Ig-variable regions and not being adjusted to the germ line (GL) sequences of human variable heavy and light chains; see FIG. 1. However, the other antibodies of the NI-202 series, in particular those with the adjusted GL sequences are structurally similar and thus can be expected to provide comparable results. These antibodies were expressed as human IgG1 molecules. The experiments in examples 3 and 4 are illustrated and described with respect to antibody NI-202.12F4 with primer induced mutations at the N-termini of the Ig-variable regions being adjusted to the germ line (GL) sequences of human variable heavy and light chains; see FIG. 1. This antibody was expressed as a chimeric molecule where the adjusted human variable domains were fused to mouse IgG2a constant regions to allow for chronic dosing studies in transgenic mouse models without to induce a mouse anti-human immune response.

Material and Methods

Detailed descriptions of conventional methods, such as those employed herein can be found in the cited literature. Unless indicated otherwise below, identification of α-synuclein-specific B cells and molecular cloning of α-synuclein antibodies displaying specificity of interest as well as their recombinant expression and functional characterization has been or can be performed as described in the Examples and Supplementary Methods section of international application PCT/EP2008/000053 published as WO2008/081008 and of PCT/EP2009/009186 published as WO2010/069603, the disclosure content of which are incorporated herein by reference in their entireties.

Purification of Antigen

Recombinant His-α-synuclein was obtained by recombinant expression in *Escherichia coli* and subsequent purification using heat induced precipitation, Nickel affinity-, anion exchange- and size exclusion-chromatography.

For example, a DNA construct comprising the cDNA encoding α-synuclein under the control of the T7 promotor was used to transform an appropriate *Escherichia coli* strain such as BL21(DE3) and expression of 200 ml cell culture was induced by the addition of 1 mM isopropyl β-D-thiogalactopyranoside (IPTG). Cells were harvested after 4 hrs induction at 37° C. and then resuspended in 20 ml 50 mM Tris, 150 mM NaCl pH 8, followed by sonication. After boiling for 15 min, the heat resistant 17000 g supernatant was collected. Similar, heat-resistant 17000 g supernatant from mock *Escherichia coli* was collected. After heat resistant 17000 g supernatant (20 ml) from *Escherichia coli* expressing His-tagged α-synuclein was adjusted to 50 mM Tris, 300 mM NaCl, 20 mM Imidazole, pH 8, it was loaded onto a HisTrap HP 1 ml (GE Life Science) column and HIS-α-synuclein was eluted with an 30-500 mM imidazole gradient. Fractions containing HIS-α-synuclein were pooled and then diluted 1:10 with 50 mM Tris pH 8. Diluted pooled fractions were applied to a HiTrap Q HP 1 ml (GE Life Science) column and bound proteins were eluted in a 30-1000 mM NaCl gradient. Finally, eluates containing HIS-α-synuclein were further purified using high performance gel filtration (Superdex 200 10/300 GL). This purification procedure yields HIS-α-synuclein with a purity grade of around 99% as estimated by SDS-PAGE and Coomassie staining. Concentration of purified protein has been determined using a BCA assay (Pierce).

α-Synuclein Antibody Screening 96 well half area Microplates (Corning) were coated with purified HIS-α-synuclein or α-synuclein (rPeptide) at a standard concentration of 2 µg/ml in coating buffer (PBS pH 9.6) overnight at 4° C. Plates were washed in PBS-T pH 7.6 and non-specific binding sites were blocked for 1 hr at RT with PBS-T containing 2% BSA (Sigma, Buchs, Switzerland). B cell conditioned medium was preabsorbed for 1 hr at RT with 10% Heat-resistant *E. coli* proteins in 1% BSA. This preabsorption step had been developed after several previous attempts of ELISA screening were unsuccessful in identifying human α-synuclein specific antibodies. Thus, fortunately it turned out that preabsorption of the ELISA plate with heat-resistant *E. coli* proteins excludes screening for false positive hits such as sticky antibodies and antibodies directed against *E. coli* protein contaminations probably present in purified recombinant α-synuclein samples. Preabsorbed medium was then transferred from memory B cell culture plates to ELISA plates and incubated for 2 hrs at RT. ELISA plates were washed in PBS-T and then incubated with horse radish peroxidase (HRP)-conjugated donkey anti-human IgG (Fcγ fragment specific) polyclonal antibodies. After washing with PBS-T, binding of human antibodies was determined by measurement of HRP activity in a standard colorimetric assay.

Molecular Cloning of α-Synuclein Antibodies

Samples containing memory B cells were obtained from volunteers >60 years of age. All volunteers had in common to lack any sign of Parkinsonism. Living B cells of selected memory B cell cultures are harvested and mRNA is prepared. Immunoglobulin heavy and light chain sequences are then obtained using Ig-framework 1 specific primers for all human variable heavy and light chain families as 5' primers in combination with primers specific for all human J segments (heavy and kappa light chain) and C segments (lambda light chain) as 3' primers (Marks et al., Mol. Biol. 222 (1991), 581-597; de Haard et al., J. Biol. Chem. 26 (1999), 18218-18230).

Identification of the antibody clone with the desired specificity is performed by re-screening on ELISA upon recombinant expression of complete antibodies. Recombinant expression of complete human IgG1 antibodies or chimeric IgG2a antibodies is achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulin are expressed by inserting the immunoglobulin heavy chain RT-PCR product in frame into a heavy chain expression vector bearing a signal peptide and the constant domains of human immunoglobulin gamma 1 or mouse immunoglobulin gamma 2a. Kappa light chain immunoglobulin is expressed by inserting the kappa light chain RT-PCR-product of NI-202.3D8 in frame into a light chain expression vector providing a signal peptide and the constant domain of human kappa light chain immunoglobulin. NI-202.12F4 and NI-202.3G12 lambda light chain immunoglobulins are expressed by inserting the lambda light chain RT-PCR-product in frame into a lambda light chain expression vector providing a signal peptide and the constant domain of human or mouse lambda light chain immunoglobulin.

Functional recombinant monoclonal antibodies were obtained upon co-transfection into HEK293 or CHO cells (or any other appropriate recipient cell line of human or mouse origin) of an Ig-heavy-chain expression vector and a kappa or lambda Ig-light-chain expression vector. Recombinant human monoclonal antibody was subsequently purified from the conditioned medium using a standard Protein A column purification.

Antibodies

Pan synuclein antibody Syn211 (Sigma) was used according to manufacturer's protocol. Recombinant human α-synuclein antibodies N1202. 21D11 and NI202.12F4 are antibodies of this invention. They were expressed in HEK293 or CHO cells and then conditioned media was directly used in subsequent applications unless otherwise stated.

Direct ELISA

Antigens were coated at indicated concentration in PBS pH 9.6 onto 96 well half area microplates (Corning) overnight at 4° C. Plates were washed in PBS-T pH 7.6 and non-specific binding sites were blocked for 1 hr at RT with PBS-T containing 2% BSA (Sigma). Probes (Primary antibodies) were then transferred to wells and incubated for 2 hrs at RT. After washing in PBS-T pH 7.6, wells were incubated with horse radish peroxidase (HRP)-conjugated polyclonal anti-human (for recombinant human antibodies), anti-rabbit (for pan synuclein antibody) or anti-mouse (for LB509 or Syn211) secondary antibodies for 1 hr at RT. After rigorous washing in PBS-T, binding of probes was determined by measurement of HRP activity in a standard colorimetric assay using 3,3',5,5'-tetramethylbiphenyl-4,4'-diamine (Sigma) as chromogenic substrate.

Peptide Scan for Epitope Mapping

The entire sequence of human α-synuclein was synthesized as overlapping peptides, with lengths of 15 amino acids (aa) and an overlap of 11 aa, coupled via a flexible linker to cellulose membrane (JPT, Berlin, Germany). A membrane that comprises a total of 33 peptides was rinsed in methanol and then blocked with Rotiblock (Roth, Karlsruhe, Germany). The membrane was incubated with indicated antibodies diluted in blocking solution and then with horse radish peroxidase (HRP)-labeled secondary antibody for 1 hr. Between incubations the membrane was washed 3× with PBS-T for 5 min. The membrane was then developed using ECL plus Western Blotting Detection Reagents (GE Healthcare).

In-Solution ELISA

NI-202.12F4 (2 µg/ml) diluted in sodium bicarbonate buffer (pH 9.6) was coated at 4° C. overnight onto ELISA plates. Then the plate was blocked with 2% BSA PBS-T and subsequently washed with PBS-T. Indicated biotinylated α-synuclein peptides were added and after 2 hrs incubation the plates were washed with PBS-T. After incubation with HRP labeled streptavidin for 1 hr, binding was determined by measurement of HRP activity in a standard colorimetric assay.

Example 1: Human Derived α-Synuclein Antibody NI-202.21D11 is Selective for Human α-Synuclein α-, β- and γ-synuclein are highly homologous proteins that are predominantly expressed in the nervous system, skeletal muscle and heart. α-synuclein is strongly linked to a broad spectrum of CNS diseases whereas β-synuclein can be a neuroprotective protein. Thus the invention provides therapeutic antibodies against pathological α-synuclein variants which do not cross react with β- and γ-synuclein. In order to support potential therapeutic use of NI-202.21D11, the antibody was tested for binding to α-, β- and γ-synuclein in a direct ELISA. Recombinant α-, β and γ-synuclein was coated onto ELISA plates at equal concentration and then either incubated with recombinant NI-202.21D11 or a control pan synuclein antibody. The pan-synuclein antibody detects all three synuclein proteins but NI-202.21D11 displays selective binding for α-synuclein (FIG. 2a).

Human and mouse α-synuclein are highly conserved proteins. To probe if recombinant NI-202.21D11 preferentially binds human vs murine α-synuclein, recombinant His-tagged human or murine α-synuclein were coated onto ELISA plates at equal concentration and then tested for NI-202.21D11 and NI-202.12F4 binding (FIG. 2b). NI-202.21D11 detects only human α-synuclein whereas NI-202.12F4 detects both human and murine α-synuclein in this direct ELISA (see PCT Publication No. WO 2010/069603 A1). Together these findings demonstrate that NI-202.21D11 is highly selective for human α-synuclein.

Figure 3:
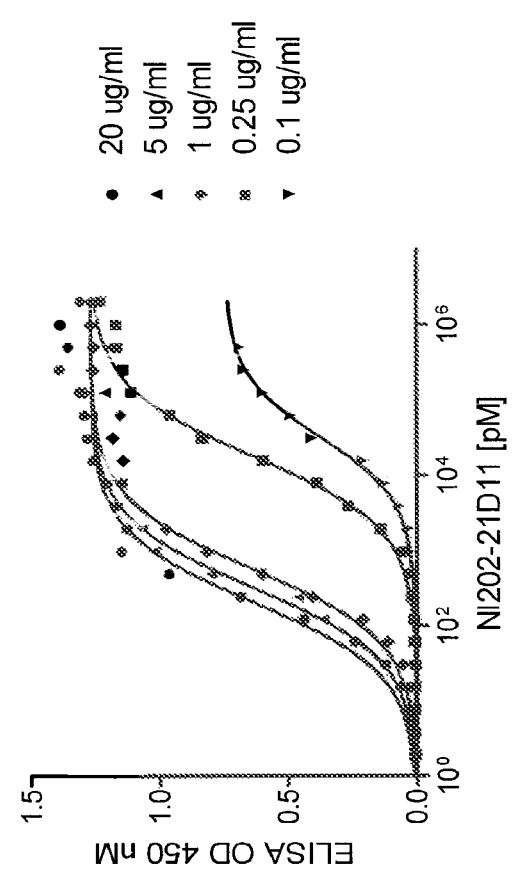
FIG. 3 Recombinant NI-202.21D11 preferentially binds to high density coated α-synuclein. Recombinant human α-synuclein was coated onto ELISA plates at indicated concentrations and probed with various concentrations of NI-202.21D11 by direct ELISA (☐ 20 µg/ml; ▲ 5 µg/ml; ◆ 1 µg/ml; ■ 0.25 µg/ml; ▼ 0.1 µg/ml). The half maximal effective concentration (EC50) indicating the potency of the antibody was determined for each coating concentration.

Example 2: NI-202.21D11 Shows Preferential Binding to Human α-Synuclein at High Coating Concentrations Pointing to a Conformational Epitope The half maximal effective concentration (EC50) indicating the potency of NI-202.21D11 was determined for low and high coating concentrations of recombinant α-synuclein using a direct α-synuclein ELISA. High affinity binding of recombinant NI-202.21D11 with an EC50 of ~200 pM was observed for high coating concentrations of α-synuclein protein (20 μg/ml). At lower concentrations of α-synuclein, a sharp decrease in affinity was observed (FIG. 3). These characteristics are in strong contrast to commercially available antibody syn211 that is also detecting an epitope in the C-terminal domain of α-synuclein. This finding suggests that NI-202.21D11 prefers an epitope that is formed or exposed under high density conditions such as found in high molecular weight species of α-synuclein.

Figure 4:
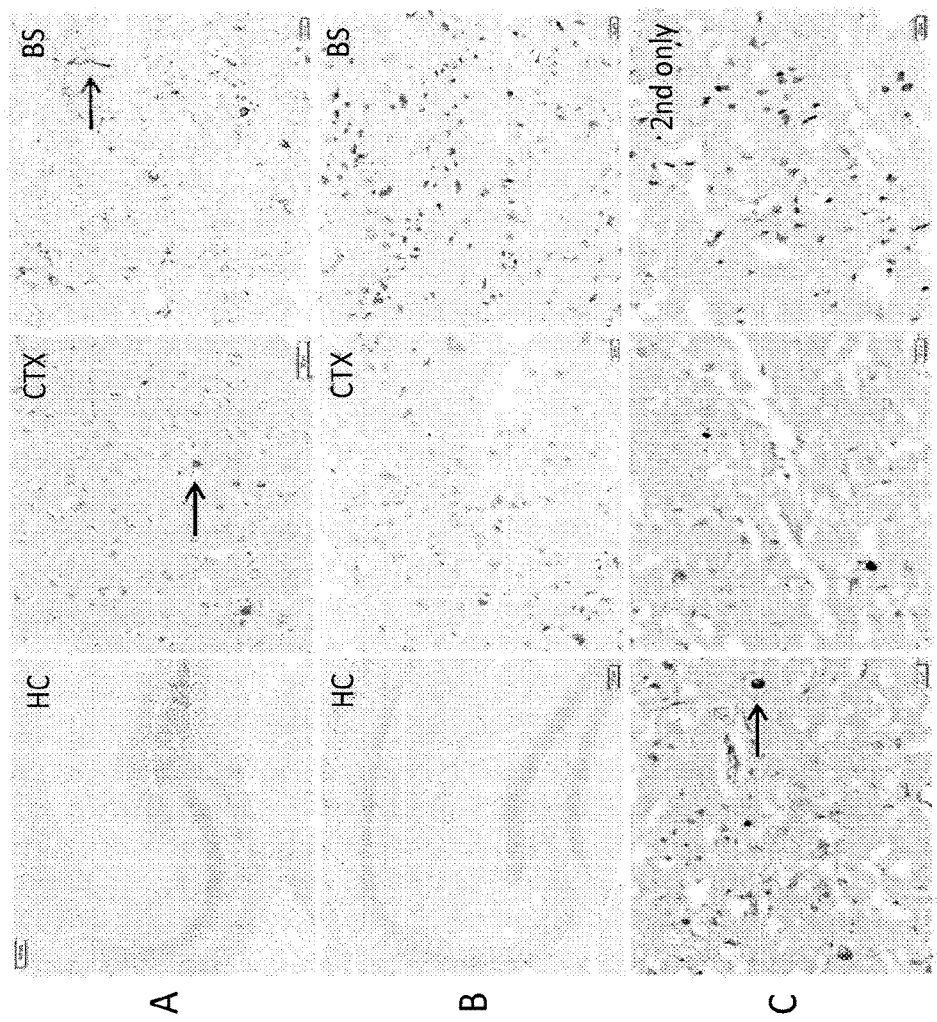
FIG. 4 Immunohistochemical binding analysis of NI-202.21D11 showed prominent staining of α-synuclein pathology including Lewy body and Lewy neurite like inclusions in paraffin sections from (A) transgenic mice overexpressing human α-synuclein A53T and (C) from human brain tissue of a Dementia with Lewy Bodies patient. (B) No staining was observed in wild-type mouse tissue and (bottom right) in a secondary antibody only control. HC=Hippocampus, CTX=Cortex, BS=Brainstem.

Example 3: Recombinant NI-202. 21D11 Binds to Pathological α-Synuclein Species in the Brain Binding of NI-202.21D11 to human α-synuclein was further characterized by immunohistochemical staining of brain sections from α-synuclein transgenic mice and from a patient with a neuropathologically confirmed synucleinopathy (Dementia with Lewy Bodies). NI-202.21D11 shows prominent staining of Lewy Body and Lewy Neurite like inclusions on Proteinase K treated paraffin sections from brain tissue of transgenic mice overexpressing human α-synuclein A53T (FIG. 4a). No NI202-21D11 staining was detected in brain sections from wild-type mice supporting that NI-202.21D11 is specific for human α-synuclein (FIG. 4b). NI-202.21D11 also detected pathological α-synuclein in human brain tissue of a patient with Dementia with Lewy Body (FIG. 4c). These results show that human-derived antibody NI-202.21D11 detects pathological α-synuclein in brain.

Figure 5:
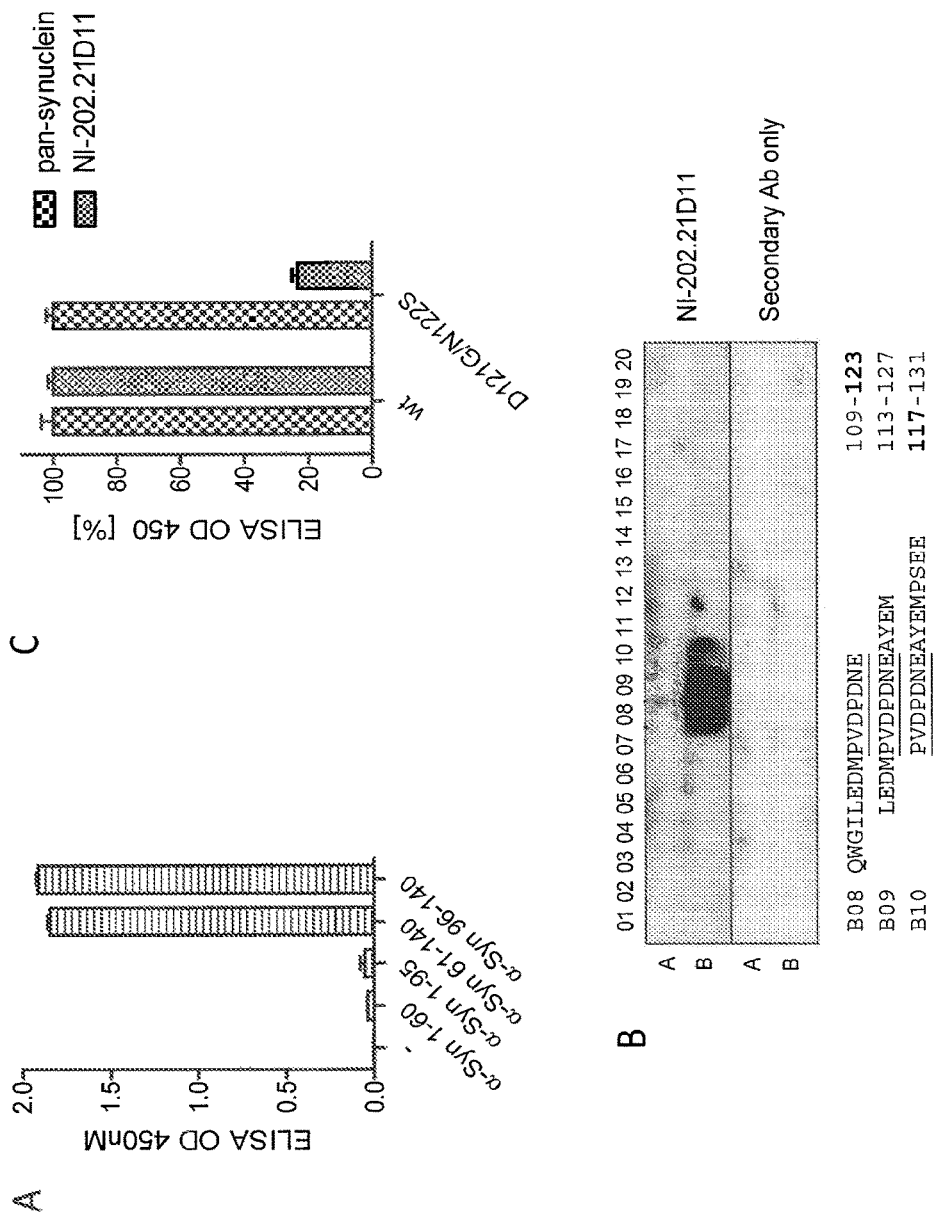
FIG. 5 Epitope mapping revealed a C-terminal binding epitope within human α-synuclein (aa 117-123 of SEQ ID NO:1) for NI-202.21D11. (A) Recombinant NI-202.21D11 bound to the C-terminal domain of human α-synuclein in a direct ELISA. α-synuclein truncations were coated onto ELISA plates at equal concentrations (2 ug/ml). NI-202.21D11 bound only to truncated α-synuclein aa 61-140 and 95-140 but not to truncations aa 1-60, 1-95. (B) Pepscan analysis showed binding of NI-202.21D11 to overlapping peptides B08 (aa 109-123 of SEQ ID NO:1), B09 (aa 113-127 of SEQ ID NO:1) and B10 (aa 117-131 of SEQ ID NO:1) of human α-synuclein suggesting that the minimal sequence required for NI-202.21D11 binding is PVDPDNE (aa 117-123 of SEQ ID NO:1) within human α-synuclein. (C) Recombinant NI-202.21D11 showed reduced binding to human α-synuclein D121G/N122S in a direct ELISA. Recombinant wt and mutated α-synuclein proteins were coated at equal concentration (2 ug/ml) onto ELISA plates and tested for recombinant NI-202.21D11 binding.

Example 4: Mapping the Epitope of Human Derived α-Synuclein-Specific Antibody NI-202. 21D11 to an Epitope within C-Terminal Domain of Human α-Synuclein α-synuclein is a 140 amino acids (aa) long natively unfolded protein that is composed of three domains. These are the N-terminal amphipathic repeat region (aa 1-60), the center region (aa 61-95) and the acidic C-terminal region (aa 96-140). (A) In order to get an initial understanding for the NI-202.21D11 binding domain, recombinant α-synuclein truncations were tested for NI-202.21D11 binding in a direct ELISA. Recombinant α-synuclein truncations from residues 1-60, 1-95, 61-140 and 96-140 were coated onto ELISA plates and then incubated with recombinant NI-202.21D11. Binding of NI-202.21D11 was only observed to α-synuclein truncations 61-140 and 96-140 demonstrating that NI-202.21D11 binds to the C-terminal acidic domain of α-synuclein (FIG. 5a).

In order to understand the recognition sequence of NI-202.21D11 in more detail, NI-202.21D11 was tested for binding to overlapping linear 15-mer peptides that cover the entire human α-synuclein amino acid sequence. Adjacent peptides share an overlap of 11 residues and peptides are C-terminally spotted to a cellulose support membrane. NI-202.21D11 bound to three overlapping peptides namely residues 109-123 of SEQ ID NO:1 (B08), 113-127 of SEQ ID NO:1 (B09) and 117-131 of SEQ ID NO:1 (B10) of human α-synuclein (FIG. 5b). This result suggests the minimal recognition sequence within the C-terminus of α-synuclein required for NI-202.21D11 binding is PVDP-DNE (residues 117-123 of SEQ ID NO:1). Notably, NI-202.21D11 bound peptide B10 slightly less than peptides B08 and B09. Thus, residues 113-117 within α-synuclein may influence on NI-202.21D11 binding.

Almost no binding of NI-202.21D11 to mouse α-synuclein was observed in a direct ELISA (FIG. 2B). Sequence alignment of the determined epitope sequence of NI-202.21D11 (PVDPDNE, residues 117-123 of SEQ ID NO:1) to the corresponding murine sequence (PVDPGSE, residues 117-123 of SEQ ID NO:2) suggest that D121 and N122 are key amino acids for selectivity of NI-202.21D11 for human vs. murine α-synuclein. In order to confirm the key role of D121N122, recombinant mutated human α-synuclein D121G/N122S was produced and tested for NI202.21D11 binding in a direct ELISA. As shown in FIG. 5c NI-202.21D11 showed almost no binding to human α-synuclein D121G/N122S compared to wt human α-synuclein. A control pan-synuclein antibody was used as normalization control for equal coating of synuclein proteins.

These results show that NI-202.21D11 is a human-derived α-synuclein antibody detecting a C-terminal epitope (residues 117-123) within human α-synuclein and that amino acids D121/N122 contribute to human vs. murine α-synuclein the selectivity.

Example 5: NI-202.12F4 Detects Epitope within α-Synuclein 4-15 and K10 in α-Synuclein is Key Amino Acid for α-Synuclein Selectivity of NI-202.12F4

Figure 6:
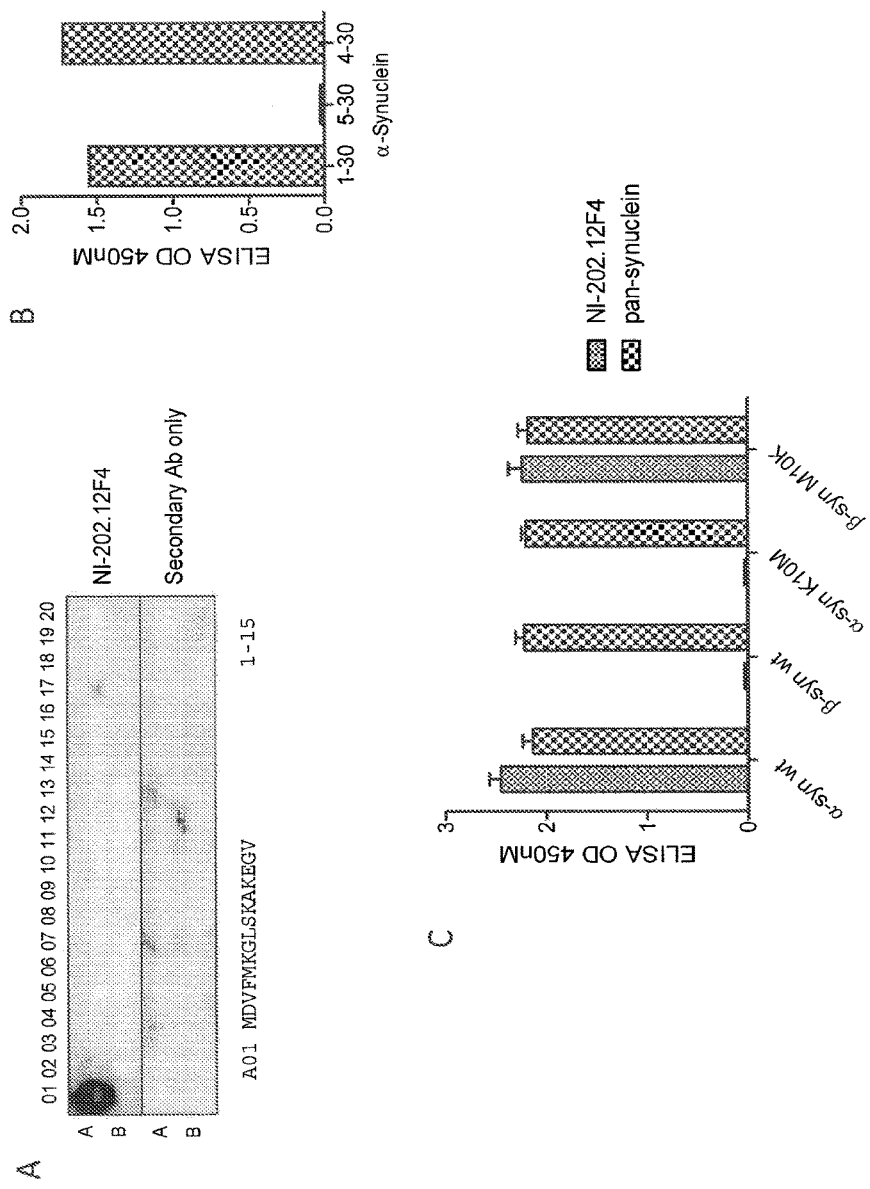
FIG. 6 NI-202.12F4 selectively binds to very N-terminus of α-synuclein. (A) Pepscan analysis shows binding of NI-202.12F4 to peptide A01 (aa 1-15 of SEQ ID NO:1) showing that the minimal recognition sequence is within residue 1-15 of α-synuclein. (B) Synthetic α-synuclein peptides from residue 1-30, 4-30 and 5-30 were tested for NI-202.12F4 binding in an in-solution ELISA. NI-202.12F4 bound aa 1-30 and 4-30 but not 5-30. This showed that NI202.12F4 epitope sequence starts at residue 4 of α-synuclein. (C) Residue K10 within NI-202.12F4 epitope is a key amino acid for selectivity of NI-202.12F4 for α-synuclein over β-synuclein. Recombinant wt and mutant α- and β-synuclein proteins were tested by direct ELISA for NI-202.12F4 binding. NI-202.12F4 bound to wt α-synuclein and mutant β-synuclein M10K but not to wt β-synuclein and mutant α-synuclein K10M. This shows that residue K10 is responsible for NI-202.12F4 α-synuclein selectivity.

In order to understand the recognition sequence (epitope) of NI-202.12F4 in more detail, overlapping linear 15-mer peptides that cover the entire human α-synuclein amino acid sequence were tested for NI-202.12F4 binding by immunoblotting. Adjacent peptides share an overlap of 11 residues and peptides were C-terminally spotted to a cellulose support membrane. NI-202.12F4 only bound to the very N-terminal peptide (A01) showing that epitope is within residues 1-15 (FIG. 6a). Since NI-202.12F4 does not bind to peptide (A02) residues 5-20, the epitope starts between residues 1 and 5. To determine the exact start residue of the epitope, synthetic α-synuclein peptides were tested for NI-202.12F4 binding in an in-solution binding ELISA. First in order to validate in-solution binding ELISA, synthetic peptides α-synuclein 1-30 and 5-30 were tested for NI-202.12F4 binding. NI-202.12F4 bound α-synuclein 1-30 but not 5-30 validating the assay by confirming the epitope starts between residue 1 and 5 (FIG. 6b). Next, α-synuclein 4-30 was tested for NI-202.12F4 binding. As show in FIG. 6b NI-202.12F4 bound to α-synuclein 4-30. These results show that NI-202.12F4 epitope starts at residue 4.

NI-202.12F4 selectively bound to α-synuclein but not β- and γ-synuclein. Sequence alignment of the NI-202.12F4 epitope containing sequence (α-synuclein 4-15) with the corresponding β-synuclein sequence showed that these sequences only differed in one amino acid. Lysine at position 10 in α-synuclein is replaced by methionine in β-synuclein. Thus NI202.12F4 should bind to β-synuclein M10K but not α-synuclein K10M. For experimental confirmation, recombinant wt and K10M α-synuclein, and wt and M10K β-synuclein were tested for NI-202.12F4 binding in a direct ELISA. As predicted NI202.12F4 only bound to wt α-synuclein and β-synuclein M10K but not to wt β-synuclein and α-synuclein K10M (FIG. 6c). A pan-synuclein antibody bound to all four recombinant proteins equally well demonstrating equal coating onto ELISA plates.

All together these experiments show that the epitope for NI202.12F4 is localized within residues 4-15 of α-synuclein. The epitope starts at residue 4 and ends between residue 11-15. Lysine at position 10 in α-synuclein accounts for the specificity of NI-202.12F4 for α-versus β-synuclein.

What is claimed is:

1. A method of treating a synucleinopathic disease in a human subject in need thereof, the method comprising administering to the human subject a therapeutically effective amount of an anti-α-synuclein antibody or α-synuclein binding fragment thereof, wherein the anti-α-synuclein antibody or α-synuclein binding fragment comprises:
    a heavy chain variable region (VH) comprising VH complementarity determining regions 1, 2, and 3 with the amino acid sequences set forth in SEQ ID NO:16, SEQ ID NO:17, and SEQ ID NO:18, respectively; and
    a light chain variable region (VL) comprising VL complementarity determining regions 1, 2, and 3 with the amino acid sequences set forth in SEQ ID NO:23, SEQ ID NO:24, and SEQ ID NO:25, respectively.

2. The method of claim 1, wherein the VH comprises the amino acid sequence set forth in SEQ ID NO:15 or SEQ ID NO:20.

3. The method of claim 1, wherein the VL comprises the amino acid sequence set forth in SEQ ID NO:22 or SEQ ID NO:26.

4. The method of claim 1, wherein the VH comprises the amino acid sequence set forth in SEQ ID NO:15 and the VL comprises the amino acid sequence set forth in SEQ ID NO:22.

5. The method of claim 1, wherein the VH comprises the amino acid sequence set forth in SEQ ID NO:20 and the VL comprises the amino acid sequence set forth in SEQ ID NO:26.

6. The method of claim 5, wherein the anti-α-synuclein antibody or α-synuclein binding fragment thereof comprises a human IgG3 heavy chain constant region and a human kappa light chain constant region.

7. The method of claim 5, wherein the anti-α-synuclein antibody or α-synuclein binding fragment thereof comprises a human IgG1 heavy chain constant region.

8. The method of claim 1, wherein the anti-α-synuclein antibody or α-synuclein binding fragment is selected from the group consisting of an Fab, an Fab', an F(ab')2, an Fd, an Fv, a single-chain Fv (scFv), a single-chain antibody, and a disulfide-linked Fv (sdFv).

9. The method of claim 1, wherein the synucleinopathic disease is Parkinson's disease, dementia with Lewy bodies, or multiple systems atrophy.

10. The method of claim 4, wherein the synucleinopathic disease is Parkinson's disease, dementia with Lewy bodies, or multiple systems atrophy.

11. The method of claim 5, wherein the synucleinopathic disease is Parkinson's disease, dementia with Lewy bodies, or multiple systems atrophy.

12. The method of claim 6, wherein the synucleinopathic disease is Parkinson's disease, dementia with Lewy bodies, or multiple systems atrophy.

13. The method of claim 1, wherein the synucleinopathic disease is Parkinson's disease.

14. The method of claim 4, wherein the synucleinopathic disease is Parkinson's disease.

15. The method of claim 5, wherein the synucleinopathic disease is Parkinson's disease.

16. The method of claim 6, wherein the synucleinopathic disease is Parkinson's disease.

* * * * *